US 11,996,172 B2

United States Patent
Mizobe

(10) Patent No.: US 11,996,172 B2
(45) Date of Patent: May 28, 2024

(54) DIAGNOSIS SUPPORT SYSTEM, INFORMATION PROCESSING METHOD, AND PROGRAM

(71) Applicant: CANON KABUSHIKI KAISHA, Tokyo (JP)

(72) Inventor: Hideaki Mizobe, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 51 days.

(21) Appl. No.: 16/592,617

(22) Filed: Oct. 3, 2019

(65) Prior Publication Data

US 2020/0035349 A1    Jan. 30, 2020

Related U.S. Application Data

(63) Continuation of application No. 15/096,097, filed on Apr. 11, 2016, now abandoned.

(30) Foreign Application Priority Data

Apr. 15, 2015   (JP) ................. 2015-083721

(51) Int. Cl.
*G16H 10/60*    (2018.01)
*G16H 30/20*    (2018.01)
(Continued)

(52) U.S. Cl.
CPC ............. *G16H 10/60* (2018.01); *G16H 30/20* (2018.01); *G16H 50/20* (2018.01); *G16H 50/70* (2018.01); *G16Z 99/00* (2019.02)

(58) Field of Classification Search
CPC ........ G16H 70/40; G16H 20/70; G16H 10/60; G16H 30/20; G16H 50/20; G16H 50/70;
(Continued)

(56) References Cited

U.S. PATENT DOCUMENTS 5,431,161 A * 7/1995 Ryals ..................... G06F 19/00
                                                      600/425
2005/0010098 A1* 1/2005 Frigstad ................. A61B 6/563
                                                      600/407
(Continued)

FOREIGN PATENT DOCUMENTS

JP      2007125240 A    5/2007
JP      2007181659 A    7/2007
(Continued)

OTHER PUBLICATIONS

Park and Chirikjian, "Interconversion between Truncated Cartesian and Polar Expansions of Images" IEEE Trans Image PRocess. Aug. 2007; 16(8): 1946-1955 (Year: 2007).*
(Continued)

*Primary Examiner* — Gregory D. Moseley
(74) *Attorney, Agent, or Firm* — Canon U.S.A., Inc. IP Division

(57) ABSTRACT

A diagnostic imaging support system that enables confirmation of abnormalities in anatomical regions of a brain includes capturing images of the brain, specifying regions in the captured images that correspond to the anatomical regions, searching a medical database for similar cases based information associated with the specified regions, and displaying the results of the search.

14 Claims, 13 Drawing Sheets

(51) Int. Cl.
  *G16H 50/20* (2018.01)
  *G16H 50/70* (2018.01)
  *G16Z 99/00* (2019.01)
(58) Field of Classification Search
  CPC .. G06F 16/148; G06F 16/90335; G06F 19/00;
  G16Z 99/00
  See application file for complete search history.

(56) References Cited

U.S. PATENT DOCUMENTS

| | | | | |
|---|---|---|---|---|
| 2005/0105828 | A1* | 5/2005 | Oosawa | G06T 19/00 |
| | | | | 382/294 |
| 2005/0114175 | A1* | 5/2005 | O'Dea | G16H 30/40 |
| | | | | 705/2 |
| 2007/0071294 | A1* | 3/2007 | Mahesh | G16H 50/20 |
| | | | | 382/128 |
| 2009/0129641 | A1* | 5/2009 | Zhou | G06T 7/11 |
| | | | | 382/128 |
| 2013/0222383 | A1* | 8/2013 | Taniguchi | A61B 6/466 |
| | | | | 345/424 |
| 2015/0212676 | A1* | 7/2015 | Khare | G06F 3/038 |
| | | | | 715/771 |
| 2015/0313480 | A1* | 11/2015 | Razavi | G16H 20/10 |
| | | | | 702/19 |

FOREIGN PATENT DOCUMENTS

| | | |
|---|---|---|
| JP | 2008-253292 A | 10/2008 |
| JP | 2013-545520 A | 12/2013 |
| JP | 5641629 B1 | 12/2014 |
| WO | 2007/114238 A1 | 10/2007 |
| WO | 2014/115065 A1 | 7/2014 |

OTHER PUBLICATIONS

Christian Thibaudeau, et al., "Fully 3D iterative CT reconstruction using polar coordinates" Med. Phys. vol. 40, No. 11, pp. 11904-1-11904-12, Nov. 2013 (Year: 2013).*

* cited by examiner

FIG. 4

$$\text{Age} = \Sigma a_i \text{Voxels}_i + \text{Intercept}$$

$$\text{Intercept} = 88.2$$

| NAME OF PART | COEFFICIENT (a) |
|---|---|
| LATERAL SULCUS ON RIGHT BRAIN SIDE | 0.91273082989 |
| LATERAL SULCUS ON LEFT BRAIN SIDE | 0.90213415169 |
| LATERAL VENTRICLE ON RIGHT BRAIN SIDE | 0.6997467195 |
| LATERAL VENTRICLE ON LEFT BRAIN SIDE | 0.70124477525 |
| WHITE MATTER IN LIMBIC SYSTEM ON RIGHT BRAIN SIDE | -1.54716146884 |
| WHITE MATTER IN LIMBIC SYSTEM ON LEFT BRAIN SIDE | -1.53568413156 |
| PONS ON RIGHT BRAIN SIDE | 1.06963294472 |
| PONS ON LEFT BRAIN SIDE | 1.02446967542 |
| CENTRAL SULCUS ON RIGHT BRAIN SIDE | 1.03660844023 |
| CENTRAL SULCUS ON LEFT BRAIN SIDE | 1.09527385627 |

# DIAGNOSIS SUPPORT SYSTEM, INFORMATION PROCESSING METHOD, AND PROGRAM

CROSS-REFERENCE TO RELATED APPLICATIONS

This application is a continuation of U.S. application Ser. No. 15/096,097, which was filed on Apr. 11, 2016 and which claims priority to Japanese Patent Application No. 2015-083721, which was filed on Apr. 15, 2015, both of which are hereby incorporated by reference herein in their entireties.

BACKGROUND

Field

Aspects of the present disclosure generally relate to a diagnosis support apparatus for a brain, a diagnosis support system, an information processing method, and a program.

Description of the Related Art

Processing in which with a use of an image obtained by imaging of an object by an image capturing apparatus such as a CT apparatus or an MRI apparatus, image regions corresponding to anatomical regions are specified in the image, and then information of characteristics of the anatomical regions is obtained has been performed. For example, a technique of measuring atrophy of parahippocampal gyrus from an MRI image obtained by imaging of a brain is disclosed in "Utility of Axial Images in an Early Alzheimer Disease Diagnosis Support System (VSRAD)", Japanese Journal of Radiological Technology, Vol. 62, No. 9, pp. 1339-1344, 2006.

However, there are various anatomical regions other than the parahippocampal gyrus in the brain, and it is difficult to confirm what abnormality is caused or to present useful information for diagnosis by comprehensively examining each of the anatomical regions.

SUMMARY OF THE INVENTION

A diagnosis support system according to an exemplary embodiment of the invention includes a specification unit configured to, based on a three-dimensional image obtained by imaging of a region including a brain of an object, specify a plurality of image regions in the three-dimensional image that correspond to a plurality of anatomical regions in the brain, a search unit configured to search a medical case database to, based on information indicating sizes of the plurality of image regions specified by the specification unit, obtain medical case information in the medical case database, and a transmission unit configured to transmit the medical case information obtained by the search unit, in which the transmitted medical case information is displayed.

Further features of aspects of the present invention will become apparent from the following description of exemplary embodiments with reference to the attached drawings.

BRIEF DESCRIPTION OF THE DRAWINGS

FIG. 4 is a diagram for explaining an age estimation formula according to the exemplary embodiment.

DESCRIPTION OF THE EMBODIMENTS

Figure 1:
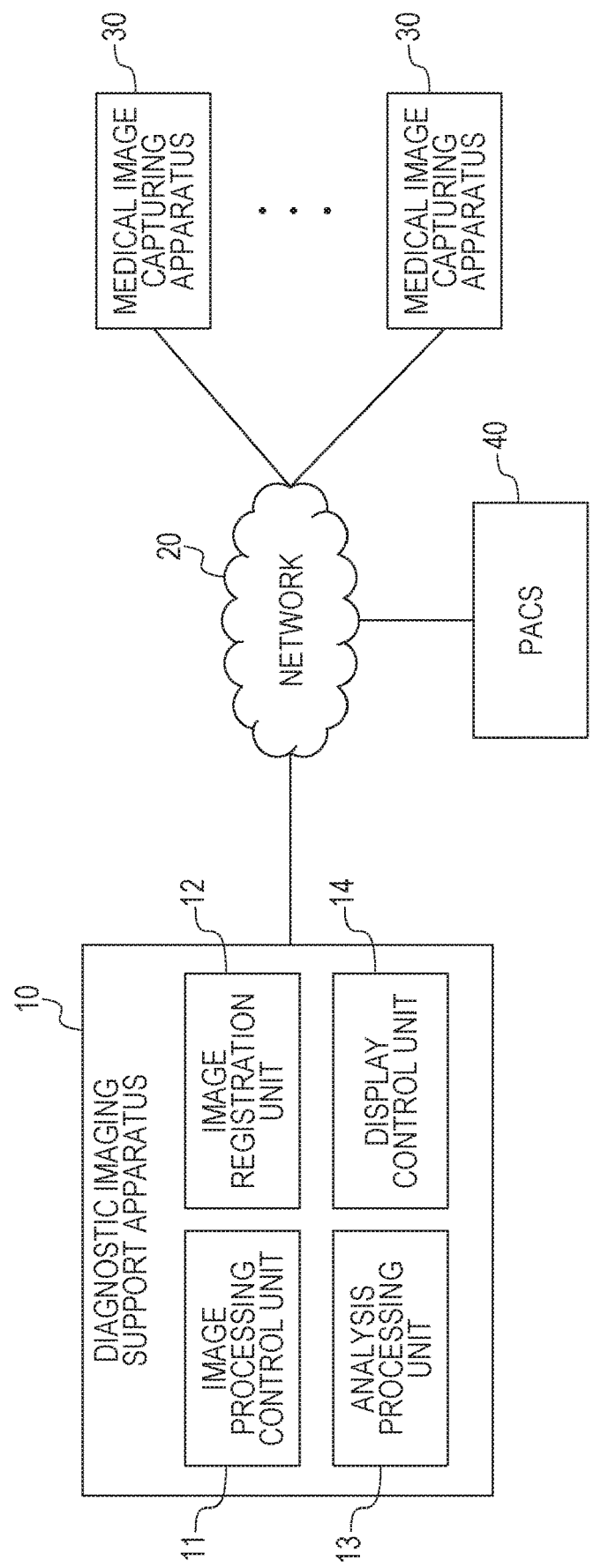
FIG. 1 is a block diagram for explaining a diagnostic imaging support system according to an exemplary embodiment.

A diagnostic imaging support system according to one of exemplary embodiments includes a diagnostic imaging support apparatus 10, a network 20, at least one medical image capturing apparatus 30, and a PACS 40. The diagnostic imaging support apparatus 10 has functions including, for example, an image processing apparatus 50, and a display apparatus 60 which will be described below. There is no limitation to such an example, and provided is a concept that diagnostic imaging support apparatus 10 also includes the image processing apparatus 50 itself which does not have the function of the display apparatus 60.

First, terms necessary for description of the exemplary embodiment of the invention will be described.

The network 20 in the first embodiment is a line by which respective apparatuses are connected, and examples thereof include a dedicated line, a local area network (LAN), a wireless LAN, and the Internet line.

The medical image capturing apparatus 30 in the exemplary embodiment is an apparatus for capturing an image used for diagnosis, and is an image capturing apparatus for capturing an image of a region including a brain of an object. Specific examples thereof include a magnetic resonance imaging (MRI) apparatus, an X-ray computed tomography (CT) apparatus, and a positron emission tomography (PET) apparatus.

The image processing apparatus 50 in the exemplary embodiment does not include a function of a display unit of the diagnostic imaging support apparatus 10, and has a configuration overlapping with a configuration of the diagnostic imaging support apparatus 10. Software which is programmed to operate various procedure described below is mounted in the image processing apparatus 50, so that a program operates or data is saved as necessary.

The PACS 40 in the exemplary embodiment refers to an image saving communication system, and is an apparatus for receiving and saving an image captured by the medical image capturing apparatus 30 or transmitting an image in response to a request from a connected apparatus. The PACS 40 includes a database in which a received image and various data associated with the image are able to be saved together.

The display apparatus 60 in the exemplary embodiment includes a screen which serves as a display unit, a touch panel, a mouse, and a keyboard which form an operation unit. Software which is programmed to operate various procedure described below is mounted in the display apparatus 60, so that a program operates or data is saved as necessary. Specifically, for example, a personal computer corresponds to the display apparatus 60.

Tomographic images in the exemplary embodiment are images which are obtained by various medical image capturing apparatuses 30 with various parameter settings and used for diagnosis. Specific examples thereof include an MR image obtained by a magnetic resonance imaging (MRI) apparatus, a CT image obtained by an X-ray computed tomography (CT) apparatus, and a positron emission tomography (PET) image obtained by a PET apparatus. Note that, the MR image may be captured by some different methods, and with the methods, tomographic images having different features, such as a T1-weighted image, a T2-weighted image, and a diffusion-weighted image may be obtained. A tomographic image is formed of one or more cross-sectional images which are two-dimensional images, and three-dimensionally represents a subject to be imaged, such as a human body, by laminating cross-sectional images captured at different positions. Normally, when a physician diagnoses presence/absence of an abnormality of a patient by observing a tomographic image, the physician uses an apparatus for displaying a group of cross-sectional images which forms the tomographic image to search for an abnormality while switching the displayed cross-sectional images one by one. Note that, since the tomographic image is obtained by laminating the cross-sectional images which are two-dimensional images and three-dimensionally represents a subject to be imaged as described above, it is possible to specify a coordinate of a certain pixel by a three-dimensional rectangular coordinate system. Specifically, the pixel is able to be specified, for example, as the pixel in an X-th column and in a Y-th row in a Z-th cross-sectional image forming the tomographic image. Accordingly, when finding certain lesions, the physician is able to record that the lesions are at a coordinate (X, Y, Z). Further, by applying that a pixel is able to be specified by a coordinate, it is also possible to specify a region with a plurality of coordinate groups, for example, in such a manner that a pixel group corresponding to a coordinate group is a cerebrum region.

A region defined image in the exemplary embodiment is a tomographic image having the same image size as that of a certain source tomographic image and is an image in which a numerical value indicating a region type, which is defined separately, is set to each pixel. Specifically, the region defined image is formed of cross-sectional images having the same number as that of the cross-sectional images forming the source tomographic image, and each of the cross-sectional images of the region defined image is formed with pixels having the same number as that of each of the cross-sectional images forming the source tomographic image. The region defined image is a tomographic image in which in a case where, for example, a bone region is defined as 1 and a cerebrum region is defined as 2 as numerical values indicating region types, when a pixel group indicated by a first coordinate group is a bone region in the source tomographic image, 1 is set to a pixel value of the pixel group indicated by the first coordinate group in the region defined image, and similarly, when a pixel group indicated by a second coordinate group is a cerebrum region in the source tomographic image, 2 is set to a pixel value of the pixel group indicated by the second coordinate group in the region defined image. That is, positions of the pixel group of the source tomographic image and positions of the pixel group of the region defined image are associated with each other by coordinates. For example, when a coordinate group of a pixel group having a pixel value of 1 in the region defined image is able to be known, a coordinate of the bone region in the source tomographic image is able to be known. Further, since 200 or more anatomical regions are defined for the head, a region defined image formed of 200 or more types of pixel value groups is created in accordance with definitions of the anatomical regions so as to allow specification of a detailed region in aspects of the invention.

An image feature quantity in the exemplary embodiment is an attribute, an index, a numerical value, or the like for indicating features of the image. Specific examples thereof include an imaging region (imaging part), an image parameter, a physical quantity, and two-dimensional and three-dimensional regions, which may be specified in the image based on anatomy, a structure, a function (for example, such as auditory cortex or visual cortex) and other criterion. For example, as regions of the head, there are the skin, the bone, the ventricle, the vein, the sulcus, the cerebrum, the cerebellum, and the like. Note that, 200 or more anatomical regions are defined for the head by medical texts or the like, and a group of the regions of the head including the skin and the bone as an example also includes anatomical regions which are defined further in detail. For example, the cerebrum is roughly formed of the cerebral cortex, the cerebral white matter, and the basal ganglion. The cerebral cortex is further subdivided into the frontal lobe, the parietal lobe, the temporal lobe, and a plurality of other anatomical regions. Examples of the physical quantity include three-dimensional positions or shapes of the respective regions, an area in any cross-sectional surface (further, an area rate to a reference region), a surface area, a volume (further, a volume rate to a reference region), an image signal intensity group for each pixel (i.e., a pixel value group), and an average image signal intensity (i.e., an average pixel value). Note that, as the image signal intensity for each pixel, different pixel values may be obtained according to differences of a manufacturer and various parameters of the image capturing apparatus, arrangement of image capturing equipment, or an object to be imaged, even if completely the same body tissue is imaged by the medical image capturing apparatus 30 of the same type. Thus, in aspects of the invention, a pixel value which is normalized is also used as the image feature quantity in order to enable comparison of pixel values for the same body tissue of a plurality of tomographic image groups. As a method of the normalization, there is a method for obtaining pixel values after linearly correcting all pixel values of a tomographic image so that an average pixel value of an air region included in the image whose image feature quantity is to be obtained, for example, an air region other than a body tissue in which stable pixel values are obtained is 0 and an average pixel value of a specific region of a table or the like of the image capturing apparatus is 500. Specifically, when an average pixel value of an air region of a certain tomographic image is 100, a pixel value of a certain pixel is 200, and an average pixel value of a specific region of a table is 300, by performing linear correction, the average pixel value of the air region is 0, the pixel value of the certain pixel is 250, and the average pixel value of the specific region of the table is 500. If a table or the like is not included in an imaging range of the tomographic image, a bone region having no abnormality may be used instead.

Figure 2:
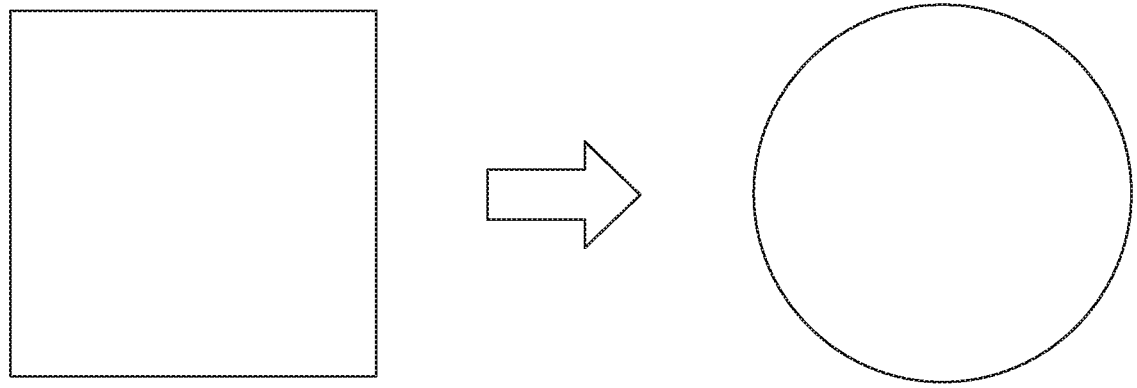
FIG. 2 is a diagram for explaining registration of two-dimensional images according to the exemplary embodiment.

Image registration processing in the exemplary embodiment refers to processing for deforming one or both of two different tomographic images so that subjects to be imaged in the images are matched as much as possible. Briefly, a deformation operation for matching a quadrangle with a circle, for example, as illustrated in FIG. 2, is also one of the image registration processing. Many methods for the image registration processing are proposed. For example, "Medical Image Registration (The BIOMEDICAL ENGINEERING Series)" authored by Joseph V. Hanja, Derek L. G. Hill, and David J. Hawks and published by CRC Press in 2001 presents a plurality of registration methods used for medical images. In particular, with processing by several nonrigid registration methods described in chapter 13, the image registration in aspects of the invention is able to be carried out. Note that, employed in the image registration processing in the exemplary embodiment for carrying out the invention is an image registration processing method using an algorithm called LDDMM (Large Deformation Diffeomorphic Metric Mapping), (Miller et al., 1993, Proceedings of the National Academy of Sciences of the United States of America, 90, 1, 194-1, 1948; Joshi et al., 1995, Geometric methods in Applied Imaging, San Diego, CA; Granander and Miller, 1996, Statistical computing and graphics newsletter, 7, 3-8). Specific use thereof will be described. In a case where a physician compares a past tomographic image and a newer tomographic image of the same patient and observes whether there is a change with a problem, even when the two tomographic images are captured by the same medical image capturing apparatus 30, the tomographic images, which are obtained from the same part, become different when a posture of the patient is different, so that the comparison becomes difficult. Thus, by performing the image registration processing for the two tomographic images and deforming one or both of the tomographic images, aspects of cross-sectional planes closely resemble to each other so that observation is easily performed when the same part is observed. Note that, normally, one of the tomographic images is deformed to be matched with the other as much as possible. On the other hand, the aforementioned deformation of both of the tomographic images is performed, for example, in a case where a reference tomographic image which serves as a reference and includes the same subject to be imaged is provided separately from the two tomographic images, and the two tomographic images are deformed so that each of the two tomographic images is matched with the reference tomographic image as much as possible, and as a result, the two tomographic images are matched with each other through the reference tomographic image. If such a method is employed, for example, when a user desires to perform observation by deforming any two tomographic images among four tomographic images to match with each other as much as possible, there are six combinations at maximum. With the method for deforming one of them, the image registration processing needs to be performed six times, but with the method for using a reference tomographic image, there is an advantage that the image registration processing only needs to be performed four times. Additionally, even when all the tomographic image groups have not been prepared, the image registration processing is able to be performed in advance with the prepared tomographic image group and the reference tomographic image, so that an effect of reducing a waiting time for the user is also achieved. In the image registration processing, deformation information for controlling how to deform the tomographic images is generated during the processing, and the tomographic images are deformed in accordance with the deformation information. Specifically, the deformation information includes information as to a pixel of which coordinate is to be moved to which coordinate, and by moving respective pixels forming the tomographic images in accordance with the deformation information, the deformed tomographic images are generated. Furthermore, there is a case where the information which is included in the deformation information and indicates a coordinate of a movement destination does not cover coordinates of all the pixels of the deformed tomographic images, and when the tomographic images are deformed as they are in accordance with the deformation information, pixels whose pixel values are not set exist in the deformed tomographic images. This case is dealt with by setting pixel values to the aforementioned pixels whose pixel values are not set based on values and positions of other pixels whose pixel values are set, with an image interpolation method such as linear interpolation. Such processing is executed by an image registration unit 12 of the diagnostic imaging support apparatus 10, or the image processing apparatus 50 described below.

Segmentation processing in the exemplary embodiment for carrying out the invention is processing for specifying one or more regions included in a tomographic image. With such processing, a plurality of image regions of a three-dimensional image that correspond to a plurality of anatomical regions in a brain, are specified. In another aspect, a first image region corresponding to a first anatomical region and a second image region corresponding to a second anatomical region not including the first anatomical region are specified in the regions in the brain included in the there-dimensional image. Such processing is executed by the image registration unit 12 of the diagnostic imaging support apparatus 10, or the image processing apparatus 50 described below. Here, the there-dimensional image may be a group of a plurality of two-dimensional tomographic images captured at different positions or may indicate three-dimensional volume data.

Though many methods are proposed for the segmentation processing, for example, as one example of a method for performing the segmentation processing for isolated lung cancer included in a chest CT image, there is a case where a region of the lung cancer is specified with a use of procedure in which by utilizing that a CT value is low in an alveoli region which is around the isolated lung cancer and includes a lot of air, and in comparison to it, the CT value is high in a lung cancer region, the region with the high CT value surrounded by the region with the low CT value is regarded as the lung cancer. Moreover, as one example of the method for performing the segmentation processing for an anatomical region of a head MR image, first, a reference head MR image and a region defined image in which an anatomical region corresponding to the head MR image is defined are prepared in advance. Then, the image registration processing is performed so that the head, as a subject to be imaged, of the head MR image to be subjected to the segmentation processing is matched with the head, as a subject to be imaged, of the reference head MR image as much as possible. At this time, the reference head MR image is deformed. Note that, deformation information for controlling what deformation is to be performed is generated when the image registration processing is performed. Further, by applying the deformation information also to the region defined image, a region defined image corresponding to the head MR image to be subjected to the segmentation processing is able to be generated. Finally, by recognizing a coordinate group having any pixel value of the generated region defined image, any region included in the head MR image to be subjected to the segmentation processing is able to be specified. In the aforementioned procedure, by preparing the reference head MR image and a region defined image in which a plurality of anatomical regions corresponding to the reference head MR image are defined, a plurality of anatomical regions of the head MR image to be subjected to the segmentation processing are able to be specified. Note that, association of a pixel value in the region defined image with a region type needs to be defined separately. For example, it is defined such that a pixel value of 1 is a bone region, and a pixel value of 2 is a cerebrum region in the region defined image. Furthermore, since 200 or more anatomical regions are defined for the head, by creating 200 or more types of definitions for associating pixel values and region types and preparing a tomographic image of the head and a region defined image corresponding thereto, 200 or more detailed regions are able to be defined with the aforementioned procedure.

Image feature quantity computation processing in the exemplary embodiment for carrying out the invention is processing which is executed by, for example, an analysis processing unit 13, and by which an image feature quantity in any region specified by the segmentation processing for a certain tomographic image is computed. Specifically, for example, regions of the bone and the cerebrum are specified by the segmentation processing for a head MR image, and a surface area and a volume of the bone region, an average pixel value of the cerebrum region, and the like are computed by the image feature quantity computation processing. Here, the analysis processing unit 13 obtains, for example, a statistical value of pixel values, values indicating shapes, and the like of a plurality of image regions corresponding to a plurality of anatomical regions in the brain, in addition to information indicating sizes thereof. Here, as the information indicating sizes, a value indicating a rate of a volume of each of the plurality of image regions normalized with a volume of a predetermined region is obtained.

Note that, in the exemplary embodiment, for example, description as an image feature quantity of a head MR image means that 200 or more anatomical regions of the head MR image are specified by segmentation processing and image feature quantity computation processing is completed for each of the regions, thus producing a state where any image feature quantity of the head MR image is able to be referred to.

Medical record information in the exemplary embodiment includes information of an object, and medical information which are stored in an apparatus for managing electronic medical record information. For example, the medical record information is attribute information of a patient or a healthy person, which is managed by an electronic medical record used in medical institutions and facilities and represented by a numerical value or a text. Examples thereof include a name, an age, a gender, a height, a body weight, a blood type, an ethnicity, a diagnosis, a medical history, a treatment history, a hospital visit record, and a result of a blood test of a patient or a healthy person. For example, the apparatus for managing an electronic medical record is connected to the network 20, and the diagnostic imaging support apparatus 10 or the image processing apparatus 50 obtains such information of an object or medical information through the network 20. Of course, such information may be stored in a memory of the diagnostic imaging support apparatus 10 or the image processing apparatus 50 in advance and obtained as necessary.

Figure 3:
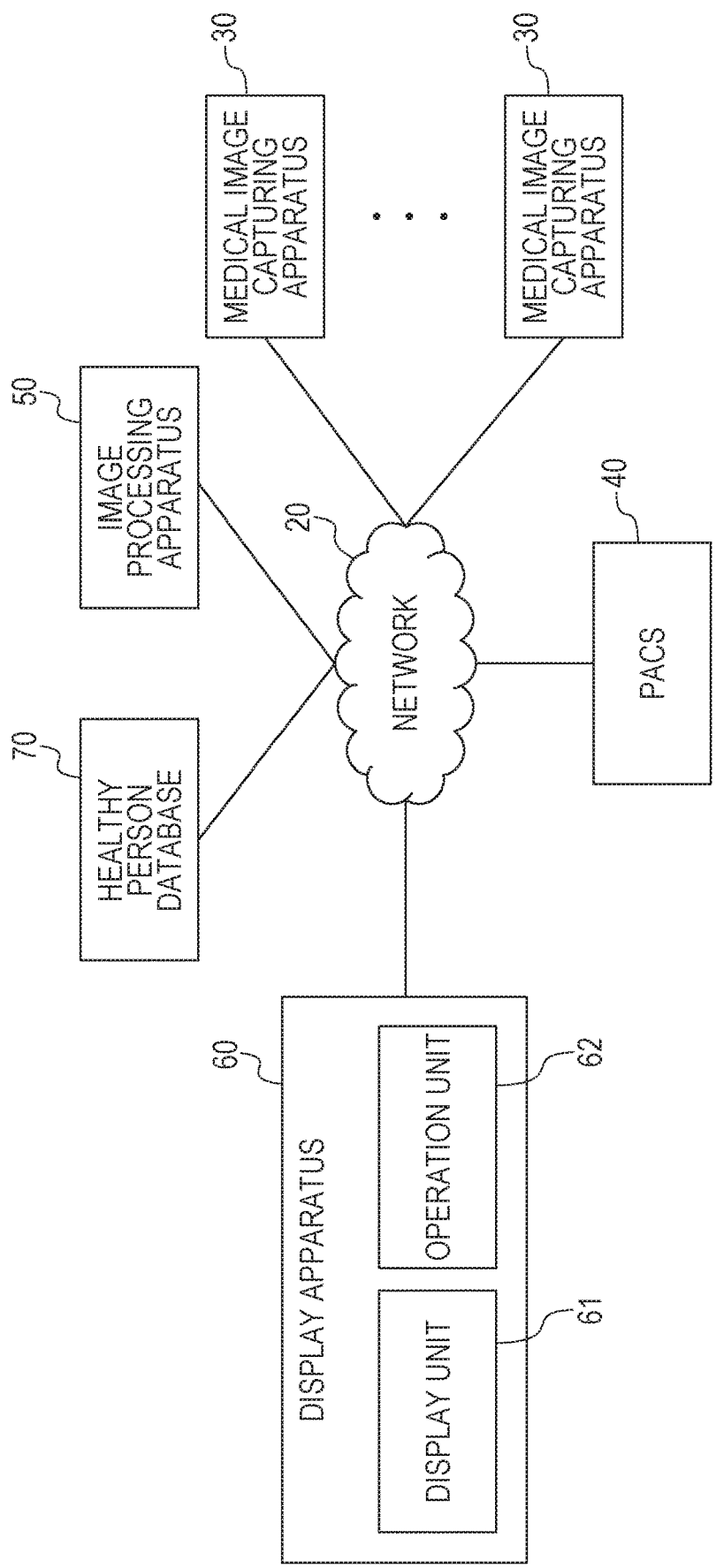
FIG. 3 is a block diagram for explaining a configuration of the diagnostic imaging support system according to the exemplary embodiment.

A diagnostic imaging support system according to the exemplary embodiment of the invention will be described below with reference to FIG. 3 and a formula 1. FIG. 3 is a bock diagram for explaining a configuration of the diagnostic imaging support system according to the present exemplary embodiment. Functional blocks may be configured as one member having the functions thereof. In addition, the functional blocks may be formed of mutually-different servers, in which the servers are connected to be communicable with each other.

The formula 1 is an example of a multiple linear regression formula by multiple linear regression analysis.

$$y = a_1 x_1 + a_2 x_2 + \text{Intercept} \qquad \text{Formula 1}$$

To give brief description, the diagnostic imaging support system according to the exemplary embodiment of the invention is a diagnostic imaging support system in which, based on information of a healthy person database 70 in which image feature quantity groups of head MR images of a healthy person group are accumulated, an age is estimated statistically by an image feature quantity group of a head MR image of an object, and the estimated age is presented to a user such as a patient, a healthy person, or a physician. Such estimation processing is realized by, for example, the analysis processing unit 13.

In the healthy person database 70 of FIG. 3, data in which an image feature quantity group of a head MR image of a healthy person is associated with medical record information including at least an age and a diagnosis of the healthy person (record as being healthy person) is comprehensively collected and saved by targeting from neonates to seniors. Further, when a query in which a condition is specified is generated by the analysis processing unit 13 and output through the network 20, the healthy person database 70 receives the query. In response to the reception, one matching the condition of the query is extracted from saved data groups, and a result of the extraction is transmitted to a transmission source of the query. Examples of the extraction by using the query include "a list of volumes of the cerebral of healthy persons whose ages are from fifty years and seven months to fifty-one years and six months" and "a list of ages and volume rates of all the regions of the head to volumes of the entire head of all the healthy persons".

In the diagnostic imaging support system according to the exemplary embodiment of the invention, by using image feature quantity groups of the data groups saved in the healthy person database 70, an age estimation formula is created and recorded in the image processing apparatus 50 in advance. By substituting an image feature quantity which is represented by a numerical value and changes by aging in the age estimation formula, an age which is statistically estimated is able to be obtained. For the age estimation formula, for example, a multiple linear regression formula by multiple linear regression analysis is able to be used. The multiple linear regression analysis is one of multivariate analysis methods and has a plurality of independent variables for the multiple linear regression analysis. The multiple linear regression formula by multiple linear regression analysis is formed of an objective variable which is desired to be estimated, an explanatory variable for deriving the objective variable, a partial regression coefficient for the explanatory variable, and a constant term. To give specific description with the formula 1, y is an objective variable, x1 and x2 are explanatory variables, a1 is a partial regression coefficient of x1, a2 is a partial regression coefficient of x2, and Intercept is a constant term (intercept). When numerical values are substituted in x1 and x2, the objective variable y which is desired to be estimated is derived. Specific numerical values need to be set to a1, a2, and Intercept of the multiple linear regression formula which is finally usable. For that purpose, a plurality of actual data groups (y, x1, x2) are substituted and a1, a2, and Intercept are set so that an error becomes the smallest by using a least-squares method or the like. The diagnostic imaging support system according to the exemplary embodiment of the invention uses a volume rate of each of 200 or more anatomical regions of the head to the entire head and ages of the medical record information among image feature quantity groups in the data groups saved in the healthy person database 70 to create an age estimation formula, and records the age estimation formula in the image processing apparatus 50. Note that, the volume rate is used to create the age estimation formula because it is qualitatively known that a part of the human brain is atrophied due to aging. In addition, not the volume of each region but the volume rate thereof to the entire head is used because as a height and a body weight vary from person to person, the volume of each of 200 or more anatomical regions of the head may vary greatly among healthy persons, even if having the same age, gender and ethnicity, so that the volume rate of each region to the volume of the entire head is used to be utilized for statistical processing in the normalized state. Note that, the age estimation formula is created by performing the multiple linear regression analysis for an extraction result of the query with the condition of "an age and a volume rate of each of all the regions of the head to a volume of the entire head of all the healthy persons" in the healthy person database 70, and the objective variable is "age" and the explanatory variable is "selection of 10 regions from 200 or more anatomical regions of the head and a volume rate thereof to the entire head". Note that, the 10 regions to be adopted for creating the age estimation formula with high accuracy based on data groups saved in the healthy person database 70 may vary depending on the data groups saved in the healthy person database 70. The 10 regions are selected with a criterion that a coefficient of determination adjusted for degree of freedom exceeds 0.75 in the multiple linear regression analysis and selected so that a significance probability of the coefficient of each explanatory variable and the constant term is lower than 1%. The number of the explanatory variables is set to 10 because though a coefficient of multiple determinations generally increases when the number of the explanatory variables increases, it is more likely that only apparent accuracy is enhanced and the number of the explanatory variables which give less influence on the objective variable is desired to be reduced. If the actual accuracy of age estimation is improved by increasing or decreasing the number of the explanatory variables, the number of the explanatory variables may not be 10. As an example of the age estimation formula, an age estimation formula as in FIG. 4 is obtained, and when a coefficient corresponding to each name of a part (partial regression coefficient) is substituted in a variable ai and a volume rate of a region corresponding to each name of a part to a volume of the entire head (explanatory variable) is substituted in VolumeRatei in the formula, an estimated age (objective variable) is obtained. Moreover, when data in which an image feature quantity group of a head MR image of a new healthy person is associated with medical record information of the new healthy person is added to the healthy person database 70, the age estimation formula may be created again, but there is a possibility that a result of age estimation changes as the age estimation formula is changed, so that attention needs to be paid. Thus, information groups of n tomographic images (info in a formula 2) are saved as the formula 2 in the healthy person database 70, and a group of x image feature quantities (feature in the formula 2) which are computed in the image feature quantity computation processing and a group of y pieces of medical record information (record in the formula 2) are included in each of the information groups.

$\{info_1, info_2, \ldots, info_n\}$ E healthy person database 70
$\{feature_{i1}, feature_{i2}, \ldots, feature_{ix}, record_{i1}, \ldots, record_{iy}\} \in info_i$
$feature_{i1} = \{rate_{i1}, \ldots, rate_{is}\}$
$feature_{ij} = ImageFeatures_{ij}$
$record_{i1} = age_i$
$record_{i2} = diagnosis_i$
$record_{ik} = MedicalRecords_{ik}$   Formula 2

The group of the x image feature quantities includes at least s image feature quantities about the volume rate (rate in the formula 2) of each of 200 or more anatomical regions (set as s regions) of the head to the entire head, and may further include an imaging region, an image parameter, three-dimensional positions or shapes of the respective regions, an area in any cross-sectional surface (further, an area rate to a reference region), a surface area, a volume (further, a volume rate to a reference region), an image signal intensity group for each pixel (i.e., a pixel value group), and an average image signal intensity (i.e., an average pixel value). The group of the y pieces of medical record information includes at least an age (age in the formula 2) and a diagnosis (diagnosis in the formula 2) (record as being a healthy person), and further may include a gender, a height, a body weight, a blood type, an ethnicity, a medical history, a treatment history, a hospital visit record, and a result of a blood test. In addition, the age estimation formula is recorded in the image processing apparatus 50. When a volume rate of p (10 in the present exemplary embodiment) regions of the head to a volume of the entire head is substituted in the age estimation formula, the estimated age is obtained.

Figure 5:
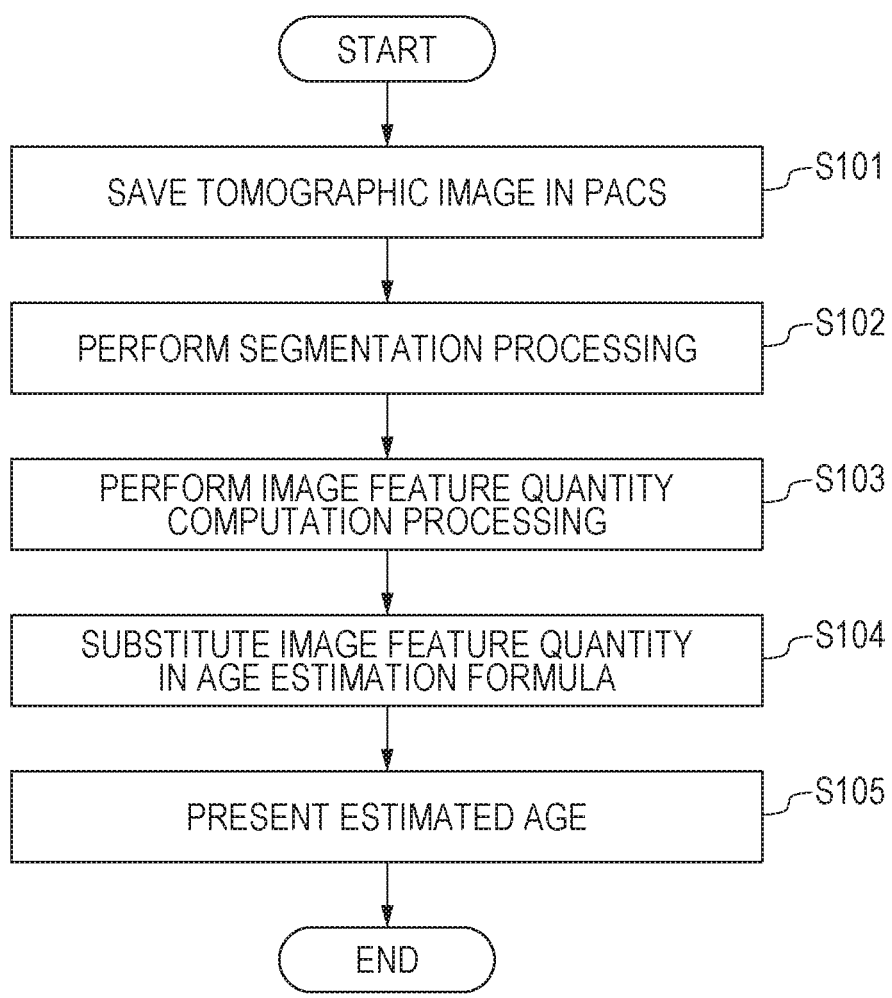
FIG. 5 is a flowchart for explaining the diagnostic imaging support system according to the exemplary embodiment.

Description will be given below for the diagnostic imaging support system according to the exemplary embodiment of the invention with reference to FIG. 5 in addition to FIG. 3. FIG. 5 is a flowchart for explaining the diagnostic imaging support system according to the exemplary embodiment of the invention.

At step S101, a head MR image of a subject whose age is desired to be estimated is captured by the medical image capturing apparatus 30, and the head MR image is saved in the PACS 40 through the network 20. When the head MR image is saved, the PACS 40 automatically transmits a start signal for image analysis processing, which includes information about a location at which the head MR image is saved, to the image processing apparatus 50 through the network 20. Note that, the start signal for image analysis processing may not be transmitted automatically by the PACS 40, and may be transmitted by another apparatus instead of the PACS 40 or may be transmitted manually by operating the display apparatus 60 by a user such as a patient, a healthy person, or a physician, as long as the head MR image is saved in the PACS 40.

At step S102, when receiving the start signal for image analysis processing, an image processing control unit 11 of the image processing apparatus 50 refers to the location at which the head MR image is saved, which is included in the start signal for image analysis processing, and reads the head MR image through the network 20. The image processing apparatus 50 performs segmentation processing for the head MR image thus read and specifies 200 or more anatomical regions.

At step S103, the image processing apparatus 50 performs image feature quantity computation processing for each of the regions specified by the segmentation processing at step S102, and records a resultant image feature quantity group in the image processing apparatus 50.

At step S104, the analysis processing unit 13 of the image processing apparatus 50 substitutes, in the age estimation formula, a volume rate of 10 regions to the entire head, corresponding to the explanatory variable of the age estimation formula, from the image feature quantity group computed by the image feature quantity computation processing at step S103, and computes an estimated age and records it in the image processing apparatus 50. Note that, since the estimated age is merely one numerical value, if a different apparatus such as the PACS 40 or the display apparatus 60 has a function of recording the estimated age, the estimated age may be recorded in the different apparatus.

At step S105, a display control unit 14 of the image processing apparatus 50 performs control so that, when the user such as the patient, the healthy person, or the physician performs a command operation for displaying the estimated age on the display apparatus 60, the display apparatus 60 reads the estimated age recorded in the image processing apparatus 50 or the different apparatus at step S104 and outputs it to the display unit 61. The display unit 61 displays information indicating the output estimated age.

Accordingly, the diagnostic imaging support system according to the exemplary embodiment is able to present a patient, a healthy person, or a physician with an age estimated from a tomographic image and to trigger a medical response such as performing medical test when an abnormal value far away from his/her actual age is presented. Though there is a method for attempting to measure a degree of aging of the brain by causing a patient or a healthy person to answer some questions in this world, the estimated age obtained by using the diagnostic imaging support system according to the exemplary embodiment may be also used as one index of the degree of aging.

Figure 6:
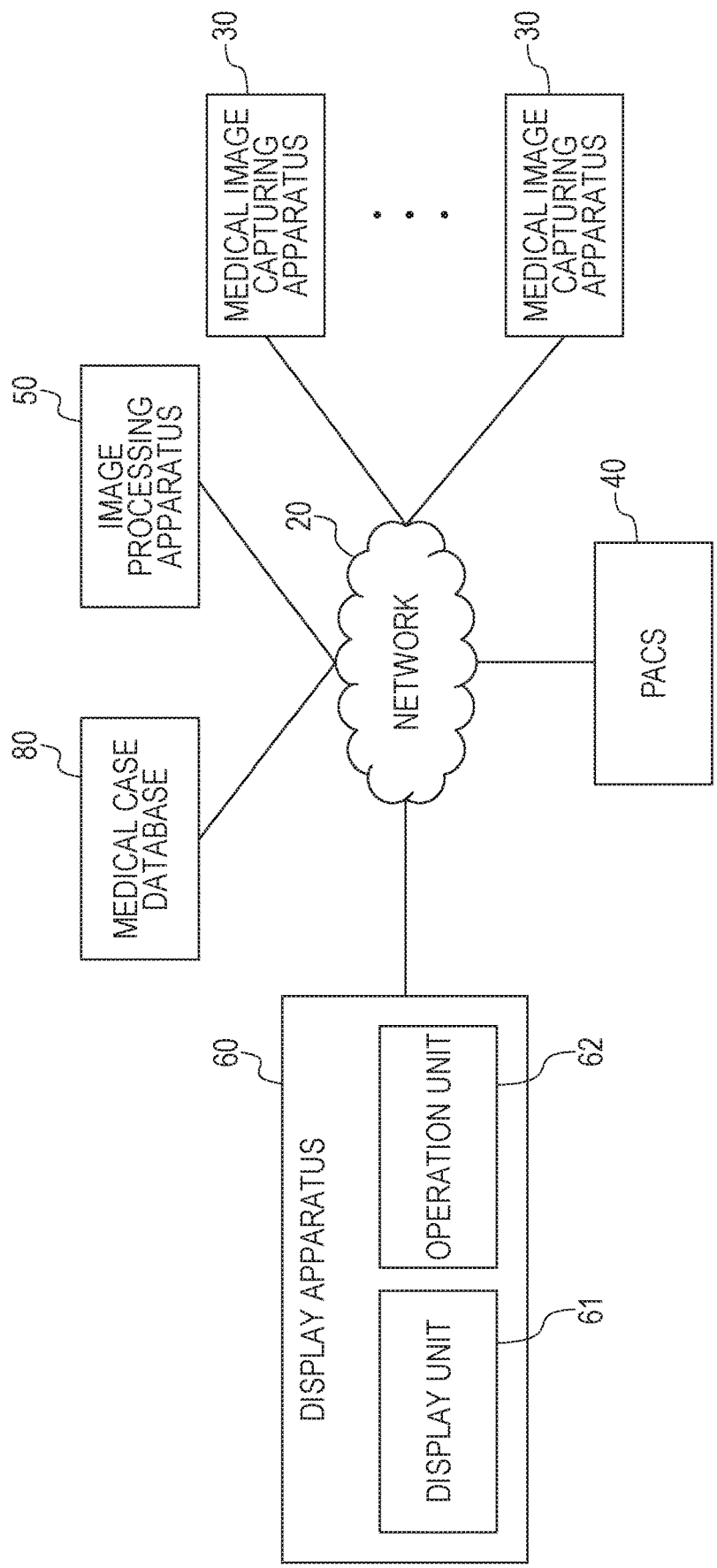
FIG. 6 is a block diagram for explaining a configuration of a diagnostic imaging support system according to a second exemplary embodiment.

A diagnostic imaging support system according to a second exemplary embodiment of the invention will be described below with reference to FIG. 6. FIG. 6 is a block diagram for explaining a configuration of the diagnostic imaging support system according to the second exemplary embodiment. Functional blocks may be configured as one member having the functions thereof. In addition, the functional blocks may be formed of mutually-different servers, in which the servers are connected to be communicable with each other.

To give brief description, the diagnostic imaging support system according to the second exemplary embodiment of the invention is a diagnostic imaging support system in which a medical case similar to an image feature quantity group of a head MR image of an object is extracted from a medical case database 80 in which image feature quantity groups of head MR images of a patient group are accumulated, and the similar medical case is presented to a user such as a patient or a physician.

Data in which an image feature quantity group of ahead MR image of a patient is associated with medical record information including at least information of a diagnosis or information of an opinion of the patient is collected and saved in the medical case database 80 of FIG. 6 by targeting from young people to elderly people. The image feature quantity group corresponds to information of characteristics regarding anatomical regions of the brain, for example, statistics of sizes or pixel values of image regions corresponding to the respective anatomical regions in the brain. The medical record information includes a diagnosis as a result of diagnostic imaging when the diagnostic imaging is completed or a determined diagnosis, for example, when a pathological test is completed. However, there is also a case where such diagnosis by the diagnostic imaging or the determined diagnosis is not provided. In this case, information of the opinion of a physician for the diagnosis may be included. The information of the diagnosis or information of the opinion is useful as similar medical case information.

The analysis processing unit 13 of the image processing apparatus 50 searches the medical case information included in the medical case database 80 to obtain a medical case similar to the medical case as a current target based on information of characteristics, for example, information of sizes of a plurality of image regions obtained by the segmentation processing by the image registration unit 12.

In a case where it is desired to present a tomographic image as information of the similar medical case to be presented to a user, the tomographic image itself used for computing the image feature quantity group or a path in which the tomographic image is saved may be saved. Further, when receiving a query in which a condition is specified, the medical case database 80 extracts one matching the condition of the query from the data groups saved therein, and transmits a result of the extraction to a transmission source of the query. Examples of the extraction based on the query include "a list of volumes of the cerebrum of patients who are diagnosed as having a Parkinson's disease, and whose ages are from fifty years and seven months to fifty-one years and six months" and "a list of volume rates of each of all the regions of the head to volumes of the entire head of all the patients with a brain disease".

The diagnostic imaging support system according to the second exemplary embodiment of the invention sets evaluation scores in advance to the data groups saved in the medical case database 80 so that data having similar features has a closer value. Specifically, main component scores of main component analysis correspond to the evaluation scores. The main component analysis will be described. The main component analysis is a method for synthesizing a plurality of variable groups common to the data groups, creating new variables (main components), and computing values of the variables (main component scores) of each data so that the data groups are able to be evaluated with the less number of variables, that is, at low dimensions. For example, when there are two variables of x1 indicating the height and x2 indicating the body weight as variables of a data group of a first person, a new variable z indicated, for example, by a formula 3 is represented by an observation variable x1 indicating the height, an observation variable x2 indicating the body weight, a main component loading amount a1 which is a coefficient of the observation variable x1, and a main component loading amount a2 which is a coefficient of the observation variable x2.

$$z = a_1 x_1 + a_2 x_2 \quad \text{Formula 3}$$

Note that, the main component loading amounts a1 and a2 are set so that the data group varies most greatly in an axis of the variable z. As a result thereof, for example, when the variable z increases in a case of the high height and the heavy body weight and the variable z decreases in a case of the low height and the light body weight on the contrary in the data group of the first person, it may be said that it is easy to rank and evaluate the data group of the first person based on a "physical size", which is an index of a body size. At this time, values of the variable z of data having close body sizes become close. Moreover, when the variable z increases in a case of the low height and the heavy body weight and the variable z decreases in a case of the high height and the light body weight on the contrary in a data group of a second person, it may be said that it is easy to rank and evaluate the data group of the second person based on a "body shape", which is an index of a fat type or a thin type. With the examples above, it is found that two new variables (main components) of the physical size and the body shape are able to be created by the two variables of the height and the body weight, and it is considered in the data group of the first person that the data group varies most greatly in an axis of the physical size, whereas not a few variations are caused also in an axis of the body shape. Thus, when the data group of the first person is analyzed in the order of greater variation, the physical size is set as a first main component and the body shape is set as a second main component in some cases. In the diagnostic imaging support system of the second exemplary embodiment of the invention, the main component analysis is performed in advance by using a volume rate of each of 200 or more anatomical regions of the head to the entire head among image feature quantity groups of the data groups saved in the medical case database 80, and resultant first main component loading amount group and second main component loading amount group, and a first main component score group and a second main component score group corresponding to each data are recorded in the image processing apparatus 50. At this time, since the main component analysis is performed by using a large amount of image feature quantity groups and the relationships between the image feature quantities are complicated, it is unable to represent features of the data groups by using the indexes represented simply by terms such as "physical size" and "body shape" as in the examples above, but it is possible to produce a state where differences between the data groups are ranked based on the main component scores statistically. Note that, when adjusting accuracy of extraction of a similar medical case, main component loading amount groups and main component score groups of a third maim component, a fourth main component, . . . , an s-th main component may be further recorded. Not the volume of each region but the volume rate thereof to the entire head is used because as the height and the body weight vary from person to person, the volume of each of 200 or more anatomical regions of the head may vary greatly among healthy persons, even if having the same age, gender and ethnicity, so that the volume rate of each region to the volume of the entire head is used to be utilized for statistical processing in the normalized state. Note that, the main component analysis is performed by targeting an extraction result of the query with the condition of "a volume rate of each of all the regions of the head to a volume of the entire head of all the patients with a brain disease" in the medical case database 80. Note that, for extracting a similar medical case with high accuracy based on the data groups saved in the medical case database 80, other image feature quantities such as a normalized average pixel value or a shape of each of all the regions of the head may be adopted in addition to the volume rate of each of all the regions of the head to the volume of the entire head. Thus, information (info in a formula 4) groups of n tomographic images are saved as in the formula 4 in the medical case database 80, and a group of x image feature quantities which are computed in the image feature quantity computation processing and a group of y pieces of medical record information are included in each of the information groups.

$\{info_1, info_2, \ldots, info_n\} \in$ medical case database 80
$\{feature_{i1}, feature_{ix}, \ldots, record_{i1}, \ldots, record_{iy}\} \in info_i$
$feature_{i1} = \{rate_{i1}, \ldots, rate_{is}\}$
$feature_{ij} = ImageFeatures_{ij}$
$record_{i1} = diagnosis_i$
$record_{ik} = MedicalRecords_{ik}$ Formula 4

The group of the x image feature quantities includes at least s image feature quantities about the volume rate of each of 200 or more anatomical regions (set as s regions) of the head to the entire head, and may further include an imaging region, an image parameter, three-dimensional positions or shapes of the respective regions, an area in any cross-sectional surface (further, an area rate to a reference region), a surface area, a volume (further, a volume rate to a reference region), an image signal intensity group for each pixel (i.e., a pixel value group), and an average image signal intensity (i.e., an average pixel value). The group of the y pieces of medical record information includes at least a diagnosis, and may further include an age, a gender, a height, a body weight, a blood type, an ethnicity, a medical history, a treatment history, a hospital visit record, and a result of a blood test. Moreover, in the image processing apparatus 50, the results corresponding to at least the first main component and the second main component (pc1 and pc2 in a formula 5) among results of the main component analysis are recorded as in the formula 5, and further results corresponding to the third main component to an s-th main component may be further recorded as necessary.

$\{pc_1, pc_2, \ldots, pc_s\}$ = results of main component analysis
$\{loading_{i1}, \ldots, loading_{is}, score_{i1}, \ldots, score_{in}\} \in pc_i$ Formula 5

The aforementioned results are formed of a group of s main component loading amounts (loading in the formula 5) and a group of n main component scores (score in the formula 5). Note that, to describe utilization of the results of the main component analysis, though details thereof will be described below, when a new tomographic image is input, a volume rate of each of the s regions of the head to a volume of the entire head (rate in a formula 6) and a main component loading amount corresponding thereto (loading in the formula 6) are multiplied with a computation method as in the formula 6, thus making it possible to compute the main component score in an i-th main component of the new tomographic image (NewScore in the formula 6).

$$NewScore_i = \sum_{j=1}^{s} loading_j \times rate_j \qquad \text{Formula 6}$$

In the present exemplary embodiment, a new main component score group is computed from the new tomographic image and is compared to the main component score groups recorded in the image processing apparatus 50 in advance, so that a tomographic image and medical record information are presented with medical cases each having a main component score group close to the new main component score group as similar medical cases. For example, medical case information having a main component score group by which an inner product value in which the new main component score group is regarded as a vector is larger than a predetermined threshold is obtained as the similar medical cases.

Note that, when the image processing apparatus 50 causes medical case information to be displayed, for example, by arranging, with an inner product value as an evaluation value, the medical case information in order from one having a larger inner product value among medical case information searched for as the similar medical cases by the method described above, more useful information is able to be displayed preferentially. Note that, in this case, the image processing apparatus 50 causes information of a diagnosis or information of an opinion for the brain by a physician, to be displayed preferentially among information included in the medical case information. This makes it possible to easily determine a diagnosis for a target medical case by referring to diagnosis and opinions of the similar medical cases.

Figure 7:
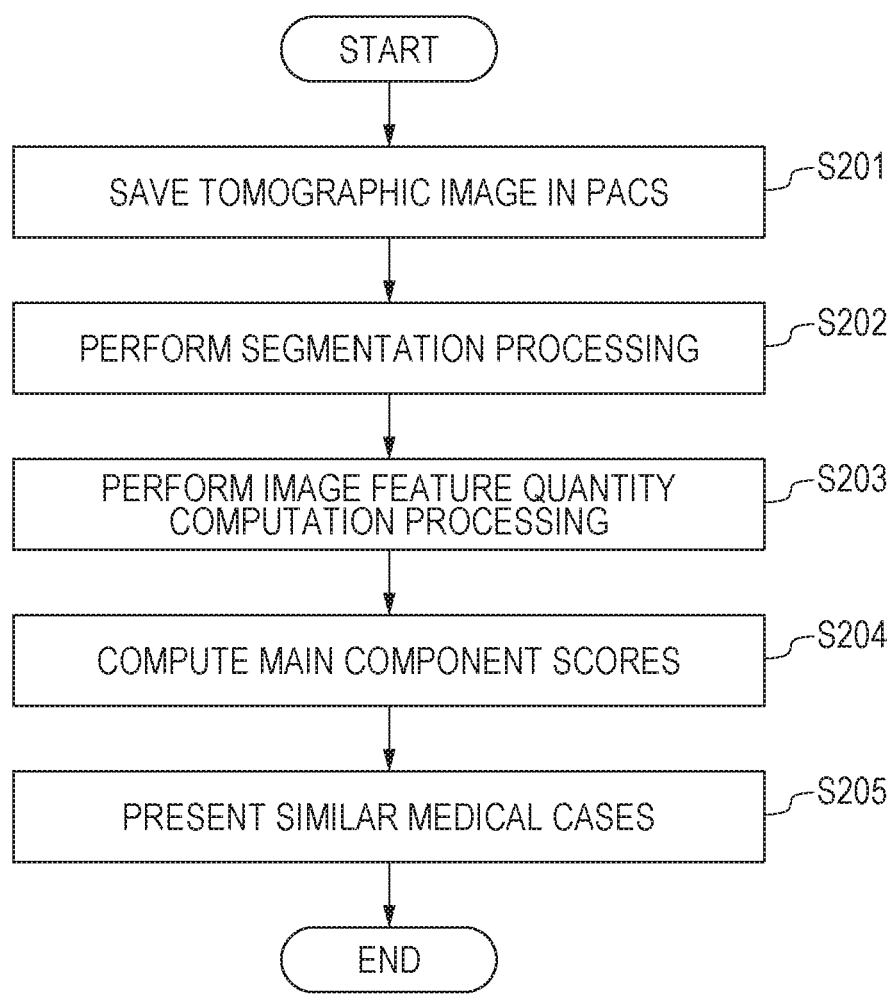
FIG. 7 is a flowchart for explaining the diagnostic imaging support system according to the second exemplary embodiment.

The diagnostic imaging support system according to the second exemplary embodiment of the invention will be described below with reference to FIG. 7 in addition to FIG. 6. FIG. 7 is a flowchart for explaining the diagnostic imaging support system according to the second exemplary embodiment of the invention.

At step S201, a head MR image of a subject for which similar medical cases are desired to be extracted is captured by the medical image capturing apparatus 30, and the head MR image is saved in the PACS 40 through the network 20. When the head MR image is saved, the PACS 40 automatically transmits a start signal for image analysis processing, which includes information about a location at which the head MR image is saved, to the image processing apparatus 50 through the network 20. Note that, the start signal for image analysis processing may not be transmitted automatically by the PACS 40, and may be transmitted by another apparatus instead of the PACS 40 or may be transmitted manually by operating the display apparatus 60 by a user such as a patient, a healthy person, or a physician, as long as the head MR image is saved in the PACS 40.

At step S202, when receiving the start signal for image analysis processing, the image processing apparatus 50 refers to the location at which the head MR image is saved, which is included in the start signal for image analysis processing, and reads the head MR image through the network 20. The image processing apparatus 50 performs segmentation processing for the head MR image thus read and specifies 200 or more anatomical regions.

At step S203, the image processing apparatus 50 performs image feature quantity computation processing for each of the regions specified by the segmentation processing at step S202, and records a resultant image feature quantity group in the image processing apparatus 50.

At step S204, the image processing apparatus 50 reads, from the image feature quantity group computed by the image feature quantity computation processing at step S203, image feature quantities corresponding to observation variables such as the volume rate, which are adopted for the main component analysis, and by using the image feature quantities and the main component loading amounts recorded in the image processing apparatus 50, computes a first main component score and a second main component score, and records them as a main component score group of the subject. In the main component analysis, if main component loading amounts and main component scores of other main components such as a third main component and a fourth component are further recorded, the main component scores corresponding thereto may be also computed and recorded in the image processing apparatus 50.

At step S205, when the user such as the patient or the physician performs a command operation for displaying similar medical cases on the display apparatus 60, the display apparatus 60 firstly transmits a signal for extraction of similar medical cases to the image processing apparatus 50. Then, the image processing apparatus 50 which has received the signal for extraction of similar medical cases through the network 20 extracts, for example, five main component score groups of the data groups, which are recorded in the image processing apparatus 50 and used for the main component analysis, in ascending order of a difference of Euclidean distances in spaces of the main component score axis with respect to the main component score group of the subject, which is recorded at step S204, and extracts data corresponding to these main component score groups as the similar medical cases from the medical case database 80. Finally, the image processing apparatus 50 transmits, to the display apparatus 60, the image feature quantities and medical record information such as diagnosis, which are associated with the similar medical cases, and the user refers to the received information. At this time, when tomographic images of the similar medical cases are also recorded in the medical case database 80, it is desirable that the tomographic images are also received by the display apparatus 60 to allow reference because the user becomes able to observe the similar medical cases in detail.

Accordingly, the diagnostic imaging support system according to the second exemplary embodiment is able to extract medical cases similar to a tomographic image of a subject from the medical case database 80 and present a user such as a patient or a physician with image feature quantities and medical record information such as diagnosis, which are associated with the medical cases. Thus, for example, in a case where the user does not have medical knowledge or does not have enough medical knowledge, when different medical record information such as a treatment history in addition to the diagnosis recorded in the medical case database 80 is recorded, the user is able to make a medical response such as diagnosis by referring to such information.

Figure 8:
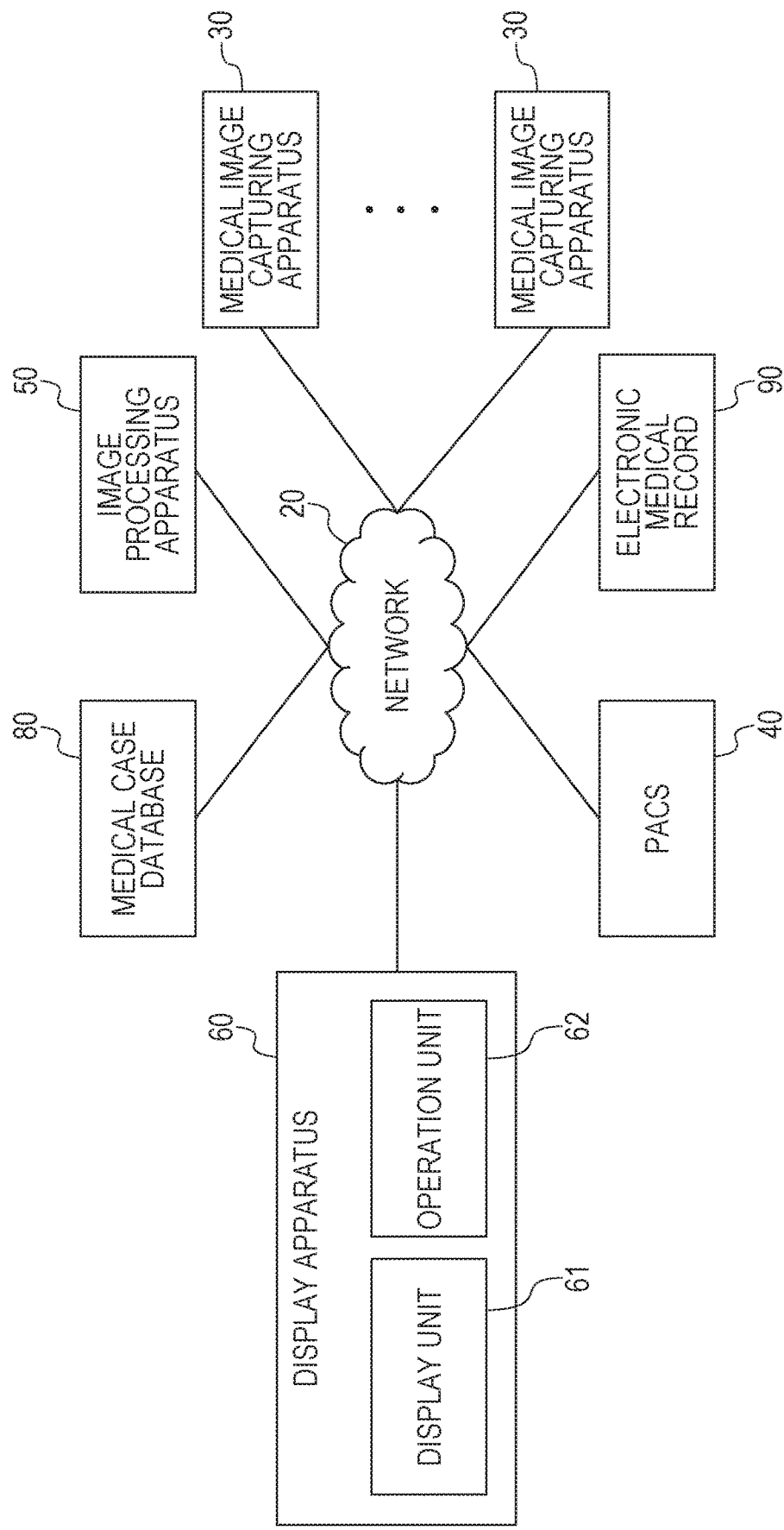
FIG. 8 is a block diagram for explaining a configuration of a diagnostic imaging support system according to a third exemplary embodiment.

A diagnostic imaging support system according to a third exemplary embodiment of the invention will be described below with reference to FIG. 8. FIG. 8 is a block diagram for explaining a configuration of the diagnostic imaging support system according to the third exemplary embodiment. Functional blocks may be configured as one member having the functions thereof. In addition, the functional blocks may be formed of mutually-different servers, in which the servers are connected to be communicable with each other.

To give brief description, the diagnostic imaging support system according to the third exemplary embodiment of the invention is a diagnostic imaging support system in which based on the medical case database 80 in which image feature quantity groups of head MR images and the like and medical record information groups of a patient group are accumulated, and an image feature quantity group of a head MR image and medical record information of a subject, a level of suspicion of one or more brain diseases with respect to the subject is presented to a user such as a patient, a healthy person, or a physician.

The medical case database 80 of FIG. 8 is similar to the medical case database 80 in the second exemplary embodiment for carrying out aspects of the invention, but needs to save therein, as each medical case information, image feature quantities indicating clinically known features, and medical record information (medical information), which are associated with medical cases, a level of suspicion of which is desired to be presented to a user such as a patient, a healthy person, or a physician. Note that, among the medical record information saved as each medical case information, information representing the known features is used for observation variables of main component analysis described below and thus needs to be able to be converted into a numerical form. For example, grade evaluation of a level of symptoms or the like is able to be used. For example, in a case of senile dementia of Alzheimer's type, five grade levels of disturbance of memory, five grade levels of aphasia, scores of a judgment test, extent of accumulation of amyloid β, a degree of reduction in blood flow of the parietal lobe, a degree of reduction in blood flow of the posterior cingulated gyrus, and the like are able to be used. Example of other medical cases saved in the medical case database 80 include Parkinson's disease, dementia with Lewy bodies, multiple system atrophy, progressive supranuclear palsy, corticobasal degeneration, Wilson's disease, normal pressure hydrocephalus, and Huntington disease. When it is desired to present the user with a tomographic image as the information of a similar medical case, the tomographic image itself used for computing the image feature quantity groups or a path in which the tomographic image is saved may be saved.

In the diagnostic imaging support system according to the third exemplary embodiment of the invention, the image feature quantities indicating clinically known features, and the medical record information group made in the numerical form, which are associated with medical cases, a level of suspicion of which is desired to be presented to a physician or the like, are selected in advance from the medical case database 80 as the observation variables for each medical case and the main component analysis is performed. That is, the main component analysis is performed with the same number of times as the number of the medical cases desired to be a subject of the presentation while changing the observation variables. Specifically, for example, in a case of senile dementia of Alzheimer's type, a volume rate of a hippocampal region to a volume of the entire head, five grade levels of disturbance of memory, five grade levels of aphasia, scores of a judgment test, extent of accumulation of amyloid β, a degree of reduction in blood flow of the parietal lobe, a degree of reduction in blood flow of the posterior cingulated gyrus, and the like are used as the observation variables in the main component analysis. The main component analysis is then performed, and resultant first main component, first main component loading amount, and first main component score corresponding to each data are recorded in the image processing apparatus 50. Note that, not the volume of the hippocampal region but the volume rate thereof to the entire head is used because as a height and a body weight vary from person to person, the volume of each of the 200 or more anatomical regions of the head may vary greatly among healthy persons, even if having the same age, gender, and ethnicity, so that the volume rate of each region to the volume of the entire head is used to be utilized for statistical processing in the normalized state. Further, in the diagnostic imaging support system according to the third exemplary embodiment of the invention, the main component having the highest contribution rate of the main components in the main component analysis is used as the first main component. Thus, information (info in a formula 7) groups of n tomographic images are saved as in the formula 7 in the medical case database 80, and a group of x image feature quantities which are computed in the image feature quantity computation processing and a group of y pieces of medical record information are included in each of the information groups.

$\{info_1, info_2, \ldots, info_n\} \in$ medical case database 80
$\{feature_{i1}, \ldots, feature_{ix}, record_{i1}, \ldots, record_{iy}\} \in info_i$
$feature_{ij} = ImageFeatures_{ij}$
$record_{ik} = MedicalRecords_{ik}$  Formula 7

At least in the group of the image feature quantities and the group of the medical record information, the image feature quantity groups indicating clinically known features, and medical record information, which are associated with d medical cases, a level of suspicion of which is desired to be presented to a physician or the like, are saved. (For description, hereinafter, a sum of the number of the image feature quantity groups indicating clinically known features of an i-th medical case desired to be a subject of presentation, and the number of the medical record information groups is set as ki.) The group of the x image feature quantities may further include an imaging region, an image parameter, three-dimensional positions or shapes of the respective regions, an area in any cross-sectional surface (further, an area rate to a reference region), a surface area, a volume (further, a volume rate to a reference region), an image signal intensity group for each pixel (i.e., a pixel value group), and an average image signal intensity (i.e., an average pixel value). The group of the y pieces of medical record information may further include an age, a gender, a height, a body weight, a blood type, an ethnicity, a medical history, a treatment history, a hospital visit record, and a result of a blood test. Moreover, in the image processing apparatus 50, a result corresponding to at least the first main component (pca in a formula 8) among results of the main component analysis using the image feature quantity groups indicating clinically known features, and the medical record information groups made in the numerical form, which are associated with d medical cases, a level of suspicion of which is desired to be presented to a physician or the like as in the formula 8 are recorded.

$\{pca_1, \ldots, pca_d\}$ = results of main component analysis of respective medical cases
$\{loading_{i1}, \ldots, loading_{ik}, score_{i1}, score_{in}\} \in pca_i$  Formula 8

The aforementioned results are formed of ki main component loading amounts (loading in the formula 8) and n main component scores (score in the formula 8). Note that, to describe utilization of the results of the main component analysis, though details thereof will be described below, when a new tomographic image is input, a group of ki numerical values (value in a formula 9) needed for the main component analysis of the i-th medical case and a main component loading amount corresponding thereto (loading in the formula 9) are multiplied by using a computation method as the formula 9 based on the result of the image feature quantity computation processing and the medical record information, thus making it possible to compute the main component score in a first main component score of the new tomographic image (NewScore in the formula 9).

$$NewScore_i = \sum_{j=1}^{k_i} loading_j \times value_j$$  Formula 9

In the present exemplary embodiment, the first main component score of the new tomographic image is computed while changing the image feature quantity group and the medical record information group needed for each of first to d-th medical cases, and d pieces of first main component score groups are computed from the new tomographic image, and the d pieces of first main component score groups are compared to the first main component score group which has been recorded before in the image processing apparatus 50, so that a level of suspicion for each medical case is computed and presented to a user such as a physician.

Figure 9:
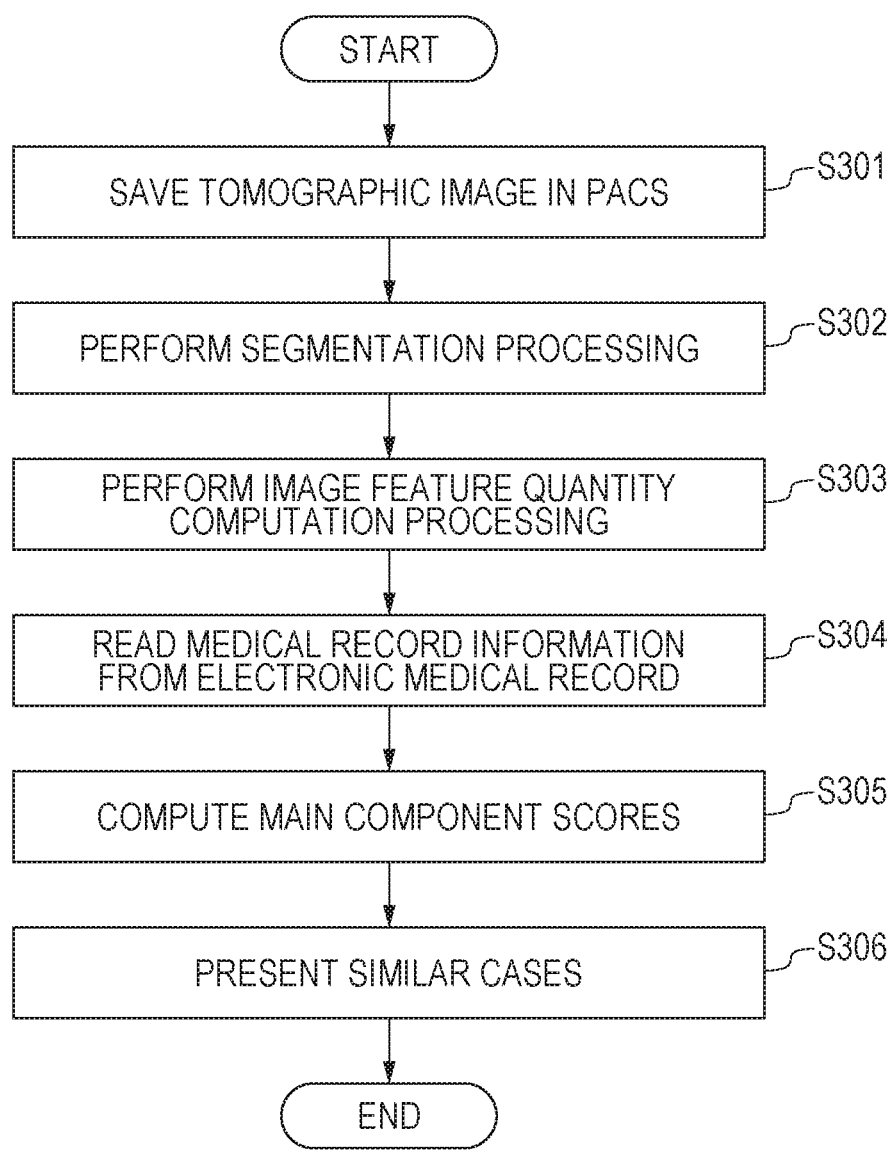
FIG. 9 is a flowchart for explaining the diagnostic imaging support system according to the third exemplary embodiment.

The diagnostic imaging support system according to the third exemplary embodiment of the invention will be described below with reference to FIG. 9 in addition to FIG. 8. FIG. 9 is a flowchart for explaining the diagnostic imaging support system according to the third exemplary embodiment of the invention.

At step S301, a head MR image of an object for which similar medical cases are desired to be extracted is captured by the medical image capturing apparatus 30, and the head MR image is saved in the PACS 40 through the network 20. When the head MR image is saved, the PACS 40 automatically transmits a start signal for image analysis processing, which includes information about a location at which the head MR image is saved, to the image processing apparatus 50 through the network 20. Note that, the start signal for image analysis processing may not be transmitted automatically by the PACS 40, and may be transmitted by another apparatus instead of the PACS 40 or may be transmitted manually by operating the display apparatus 60 by a user such as a patient, a healthy person, or a physician, as long as the head MR image is saved in the PACS 40.

At step S302, when receiving the start signal for image analysis processing, the image processing apparatus 50 refers to the location at which the head MR image is saved, which is included in the start signal for image analysis processing, and reads the head MR image through the network 20. The image processing apparatus 50 performs segmentation processing for the head MR image thus read and specifies 200 or more anatomical regions.

At step S303, the image processing apparatus 50 performs image feature quantity computation processing for each of the regions specified by the segmentation processing at step S302, and records resultant image feature quantity groups in the image processing apparatus 50.

At step S304, the image processing apparatus 50 reads, from an electronic medical record 90, all the medical record information adopted in the main component analysis among the medical record information of the object.

At step S305, the image processing apparatus 50 reads, from the image feature quantity groups computed by the image feature quantity computation processing at step S303, the image feature quantity group corresponding to the observation variables such as the volume rate and the medical record information group read at step S304, which are adopted for the main component analysis, with respect to each of the medical cases desired to be a subject of the presentation, and by using the image feature quantity group and the medical record information group thus obtained, and the first main component loading amount recorded in the image processing apparatus 50, computes a first main component score and records it in the image processing apparatus 50 as the first main component score of the object. That is, the first main component score of the object corresponding to each of the medical cases desired to be a subject of the presentation is recorded in the image processing apparatus 50.

At step S306, when the user such as the patient, or the physician performs a command operation for displaying the level of suspicion of one or more brain diseases on the display apparatus 60, the display apparatus 60 firstly transmits a signal for computation of the suspicion level of the brain diseases to the image processing apparatus 50. Then, the image processing apparatus 50 which has received the signal for computation of the suspicion level of the brain diseases through the network 20 linearly computes the score of the first main component of the object, which is recorded at step S305, when the maximum first main component score and the minimum first main component score, which are computed in advance, of the respective medical cases desired to be a subject of the presentation are 100 and 0, respectively, and records the score thus obtained as the suspicion level in the image processing apparatus 50. For example, in a case where the maximum first main component and the minimum first main component in the senile dementia of Alzheimer's type, which are recorded in the image processing apparatus 50, are 2 and −2, respectively in the main component analysis, when the first main component of the object is 1, 75 is recorded as the suspicion level. The suspicion levels of other medical cases which are desired to be a subject of the presentation are similarly computed and recorded. Finally, the image processing apparatus 50 transmits the suspicion levels of the medical cases which are desired to be a subject of the presentation to the display apparatus 60 and the display apparatus 60 displays the suspicion levels. Note that, the suspicion levels may be computed and displayed in a different manner according to a purpose.

Accordingly, the diagnostic imaging support system according to the third exemplary embodiment allows a user such as a patient or a physician to confirm suspicion levels of one or more brain diseases for an object. Thus, for example, in a case where the user does not have medical knowledge or does not have enough medical knowledge, the user is able to make a medical response such as diagnosis by referring to the suspicion levels.

A projection image in a fourth exemplary embodiment for carrying out aspects of the invention is a MIP (Maximum Intensity Projection) image or a MinIP (Minimum Intensity Projection) image, serving as a two-dimensional image generated from a tomographic image. The projection image is an image obtained by projecting all pixels of cross-sectional images, which form the tomographic image saved in the PACS 40, in a direction of sight line around an axis running perpendicularly. Specifically, in a case where a tomographic image formed by one or more axial images as cross-sectional images is set as a subject, when a direction in which the axial images are laminated is a Z-axis in a three-dimensional rectangular coordinate system (in a coordinate system of X-, Y-, and Z-axes), by setting a vector in the direction of sight line as $(X, Y, Z)=(-\sin \theta, -\cos \theta, 0)$ with the vector in the direction of sight line as $(X, Y, Z)=(0, 0, -1)$ and setting $\theta$ to be 0 or more and less than $2\pi$ ($\pi$ is a circular constant), a projection image is created while projecting all the pixels. That is, by changing $\theta$, the projection image in which a subject to be imaged rotates with the Z-axis direction as a rotation axis is obtained. Furthermore, when $\theta$ is 0, the projection image in the coronal direction is obtained, and when $\theta$ is $\pi/2$, the projection image in the sagittal direction is obtained. The projection image may be generated with a method of volume rendering, surface rendering or the like for the subject to be imaged.

Figure 10:
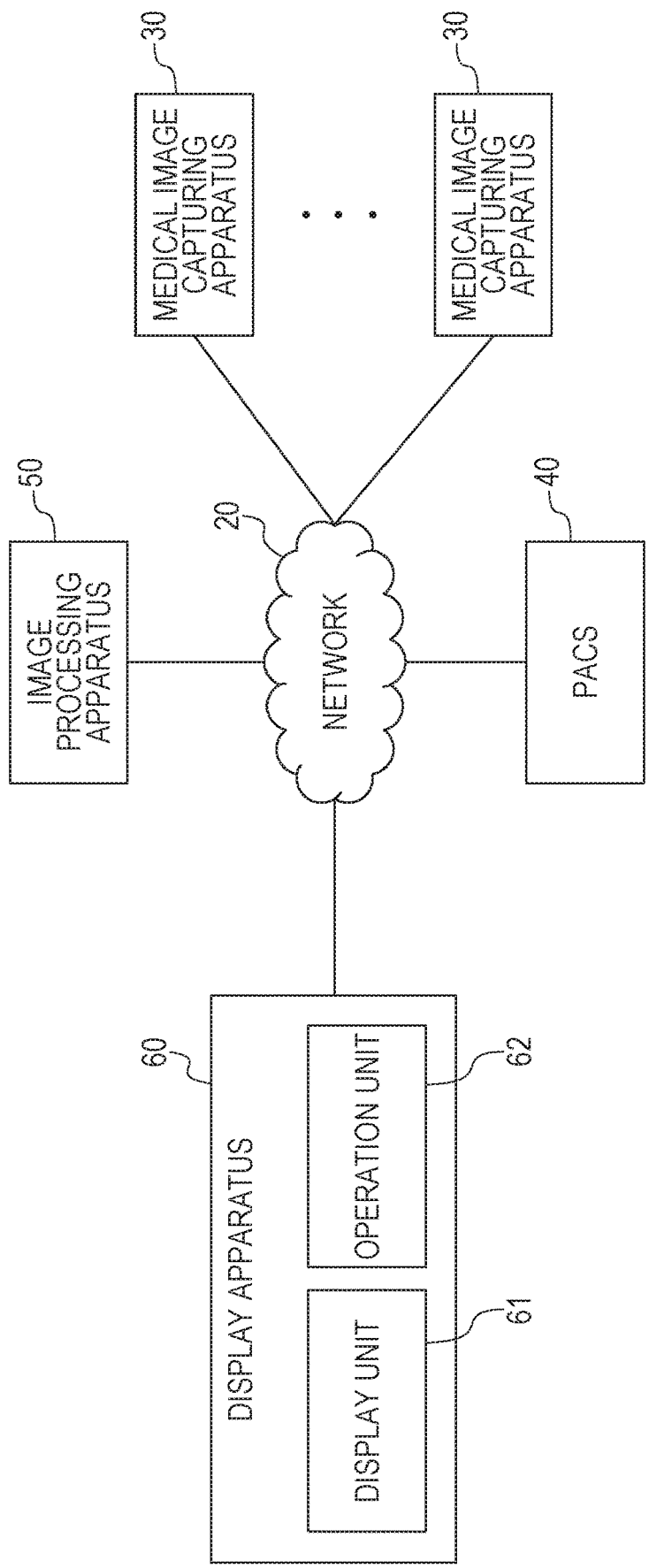
FIG. 10 is a block diagram for explaining a configuration of a diagnostic imaging support system according to a fourth exemplary embodiment.

A diagnostic imaging support system according to a fourth exemplary embodiment of the invention will be described below with reference to FIG. 10. FIG. 10 is a block diagram for explaining a configuration of the diagnostic imaging support system according to the fourth exemplary embodiment. Functional blocks may be configured as one member having the functions thereof. In addition, the functional blocks may be formed of mutually-different servers, in which the servers are connected to be communicable with each other.

To give brief description, the diagnostic imaging support system according to the fourth exemplary embodiment of the invention is a diagnostic imaging support system for providing a display method and an operation method suitable for comparing and observing tomographic images, in which display of a difference image between two tomographic images saved in the PACS 40 is rotated and a coordinate of any pixel of the difference image is further specified by a user to thereby display a cross-sectional image at a position thereof.

Figure 11:
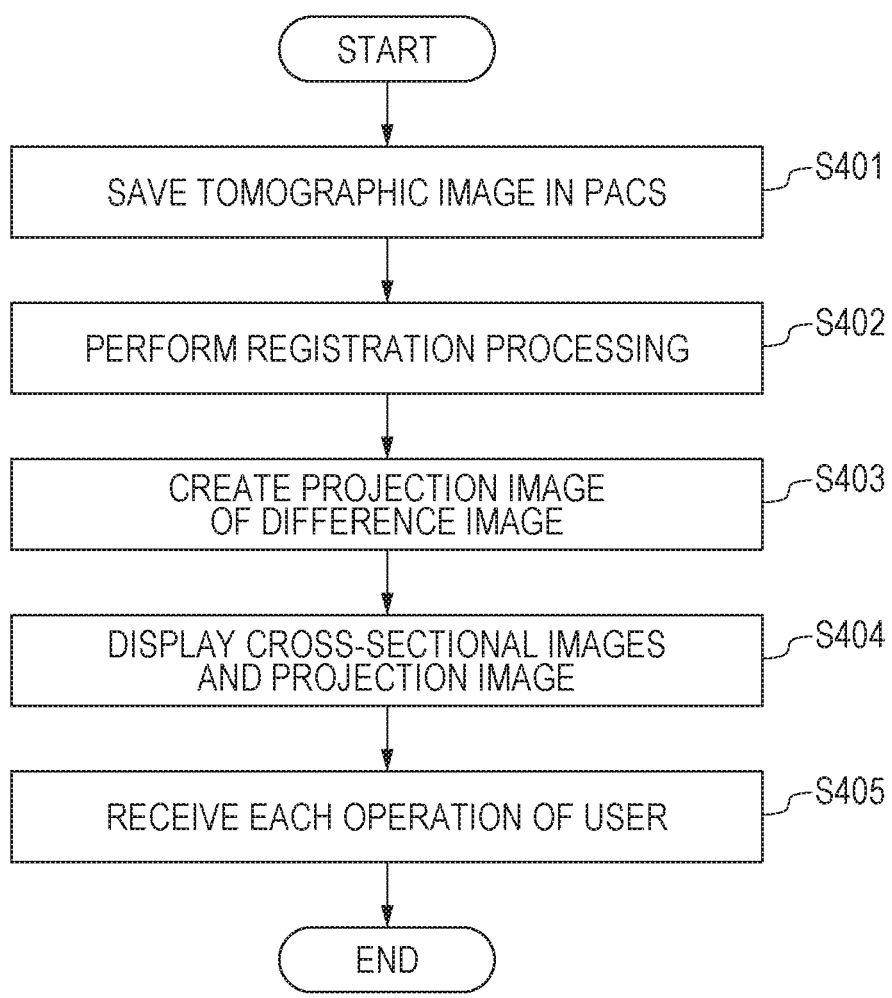
FIG. 11 is a flowchart for explaining the diagnostic imaging support system according to the fourth exemplary embodiment.

The diagnostic imaging support system according to the fourth exemplary embodiment of the invention will be described below with reference to FIG. 11 in addition to FIG. 10. FIG. 11 is a flowchart for explaining the diagnostic imaging support system according to the fourth exemplary embodiment of the invention. Note that, description will be given in the fourth exemplary embodiment of the invention for a case where two tomographic images obtained by imaging of the same part of the same patient or the same healthy person (hereinafter, referred to as a subject) by the medical image capturing apparatuses 30 of the same type are compared and observed.

At step S401, a tomographic image of a subject, which is desired to be a subject of comparison and observation, is captured by the medical image capturing apparatus 30, and the tomographic image is saved in the PACS 40 through the network 20. When the tomographic image is saved, the PACS 40 automatically transmits, to the image processing apparatus 50 through the network 20, a start signal for image analysis processing, which includes information about locations at which the tomographic image and a past tomographic image including the same part to be imaged as that of the tomographic image are saved. Note that, the start signal for image analysis processing may not be transmitted automatically by the PACS 40, and may be transmitted by another apparatus instead of the PACS 40 or may be transmitted manually by operating the display apparatus 60 by a user such as a patient, a healthy person, or a physician, as long as the tomographic image and the past tomographic image are saved in the PACS 40.

At step S402, when receiving the start signal for image analysis processing, the image processing apparatus 50 refers to the locations at which the tomographic image and the past tomographic image are saved, which are included in the start signal for image analysis processing, and reads a group of the tomographic images through the network 20. The image processing apparatus 50 performs registration processing and deforms the group of the tomographic images thus read so that the two tomographic images are matched with each other as much as possible. The image processing apparatus 50 saves, in the PACS 40, the deformed tomographic images, which are generated by the image registration processing. Note that, for the sake of convenience of description, only the past tomographic image of the group of the tomographic images is deformed in the diagnostic imaging support system according the fourth exemplary embodiment of the invention. When it is not desired that the deformed tomographic image is saved in the PACS 40 depending on a situation, it may be set that deformation information generated by the image registration processing is saved in the image processing apparatus 50 or the PACS 40, and when an apparatus such as the display apparatus 60 requests a deformed image, by applying the deformation information to the corresponding tomographic image, an image which is temporarily deformed is created and transmitted to the apparatus.

At step S403, when a user such as a physician performs a command operation for displaying the group of the tomographic images by operating the display apparatus 60, the display apparatus 60 firstly transmits, to the PACS 40, a signal for requesting the group of the tomographic images through the network 20, and the PACS 40 transmits, to the display apparatus 60, the tomographic image captured at step S401 (hereinafter, referred to as a first tomographic image) and the deformed tomographic image saved in the PACS 40 at step S402 (hereinafter, referred to as a second tomographic image) of the group of the tomographic images in response to the signal. The display apparatus 60 then creates a difference image by performing subtraction between pixel values of pixels at corresponding pixels of the first tomographic image and the second tomographic image, and further creates a projection image thereof. Note that, the processing for creating the difference image and the projection image described above may be omitted by creating the difference image and the projection image in advance by the image processing apparatus 50 and further saving them in the PACS 40 so that they are read by the display apparatus 60 at a time point of step S402.

Figure 12:
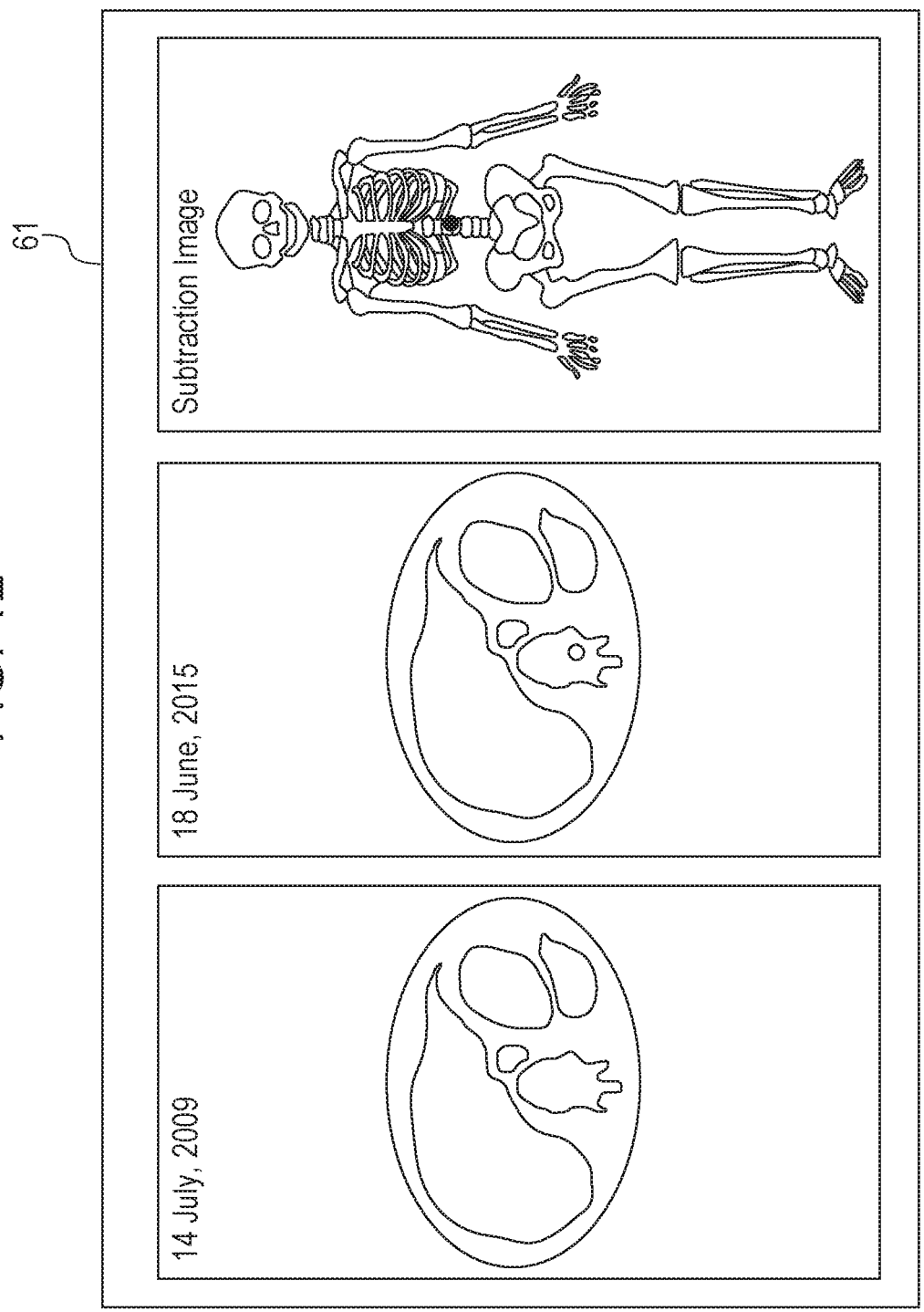
FIG. 12 is a diagram for explaining display contents displayed on a display unit of the diagnostic imaging support system according to the fourth exemplary embodiment.

At step S404, the projection image created at step S403 is displayed on the display unit 61. A state at this time is illustrated in FIG. 12, in which a cross-sectional image of the past deformed tomographic image as the second tomographic image, a cross-sectional image of the latest tomographic image captured at step S401 as the first tomographic image, and the projection image of the difference image created at step S403 are displayed from the left. Note that, when the tomographic images in the group are matched with each other completely after the deformation by the registration processing at step S402, the difference image at step S403 has a pixel value of 0 for all the pixels, but there is a difference actually due to the change of the subject to be imaged or lack of accuracy of the registration processing, and a rough shape of the subject whose image is captured is visually recognized in the projection image of the difference image in many cases. Display of the projection image is updated while changing θ in the vector in the direction of sight line at a constant time interval. That is, a portion of the display unit 61, on which the projection image is displayed, corresponds to a moving image by rotational display in which the rough shape of the subject continues to rotate with an axis of ordinates as a rotational axis. At the portion of the display unit 61, on which the projection image is displayed, the display is provided as if a transparent human body rotates, so that a shape of the human body is easily recognized, and further, a part with abnormality is displayed more densely, so that a three-dimensional position of the part with abnormality in the human body is easily recognized.

At step S405, when the user places a mouse pointer on the portion of the display unit 61, on which the projection image is displayed, by an operation unit 62, such as a mouse, connected to the display apparatus 60 or when a focus is moved to the portion where the projection image is displayed, the update of the projection image explained at step S404 is stopped in order to receive each operation of the user. That is, the display of the moving image is temporarily stopped so that the rotational display of the projection image appears to be stopped for the user. At this time, θ in the vector in the direction of sight line may be changed to update display with a wheel operation of a mouse, any key operation of a keyboard, or the like by the operation unit 62 connected to the display unit 61. That is, the user is able to operate rotation and stop of the rotational display. When any coordinate of the projection image is specified by the operation unit 62 connected to the display apparatus 60, the display apparatus 60 updates the cross-sectional image of the first tomographic image and the cross-sectional image of the second tomographic image at step S404. Specifically, the projection image is a two-dimensional image, and a Y coordinate serving as a vertical direction of a pixel group forming the projection image corresponds to the Z coordinate of the group of the tomographic images. Therefore, for example, when the part with abnormality, which is displayed more densely on the portion where the projection image is displayed, is clicked (specified) by the operation unit 62, such as the mouse, connected to the display apparatus 60, the Y coordinate in the projection image and the Z coordinate in the group of the tomographic images are specified, and the display apparatus 60 updates the cross-sectional image of the first tomographic image and the cross-sectional image of the second tomographic image, which are displayed at step S404, respectively to Z-th cross-sectional images. That is, by clicking the part with abnormality such as a cancer, which is displayed more densely on the projection image, the user is able to observe the abnormal part on the cross-sectional images, so that time and effort so far for an operation of switching the cross-sectional images becomes unnecessary. Further, since the aforementioned switching of the cross-sectional images in the group is performed in response to pressing of a button of the mouse serving as the operation unit 62 connected to the display apparatus 60, a dragging operation of the mouse in a vertical direction on the projection image may also serve as an operation of switching the cross-sectional image of the first tomographic image and the cross-sectional image of the second tomographic image simultaneously and successively.

Accordingly, the diagnostic imaging support system according to the fourth exemplary embodiment is able to present a user such as a physician with a difference between two tomographic images in a group so as to be recognized in a three-dimensional manner by rotating display of a projection image of the difference image. Further, since the cross-sectional images having a difference are able to be displayed instantly when the user operates the projection image, reduction of a fatigue at a time of comparison and observation can be expected.

Figure 13:
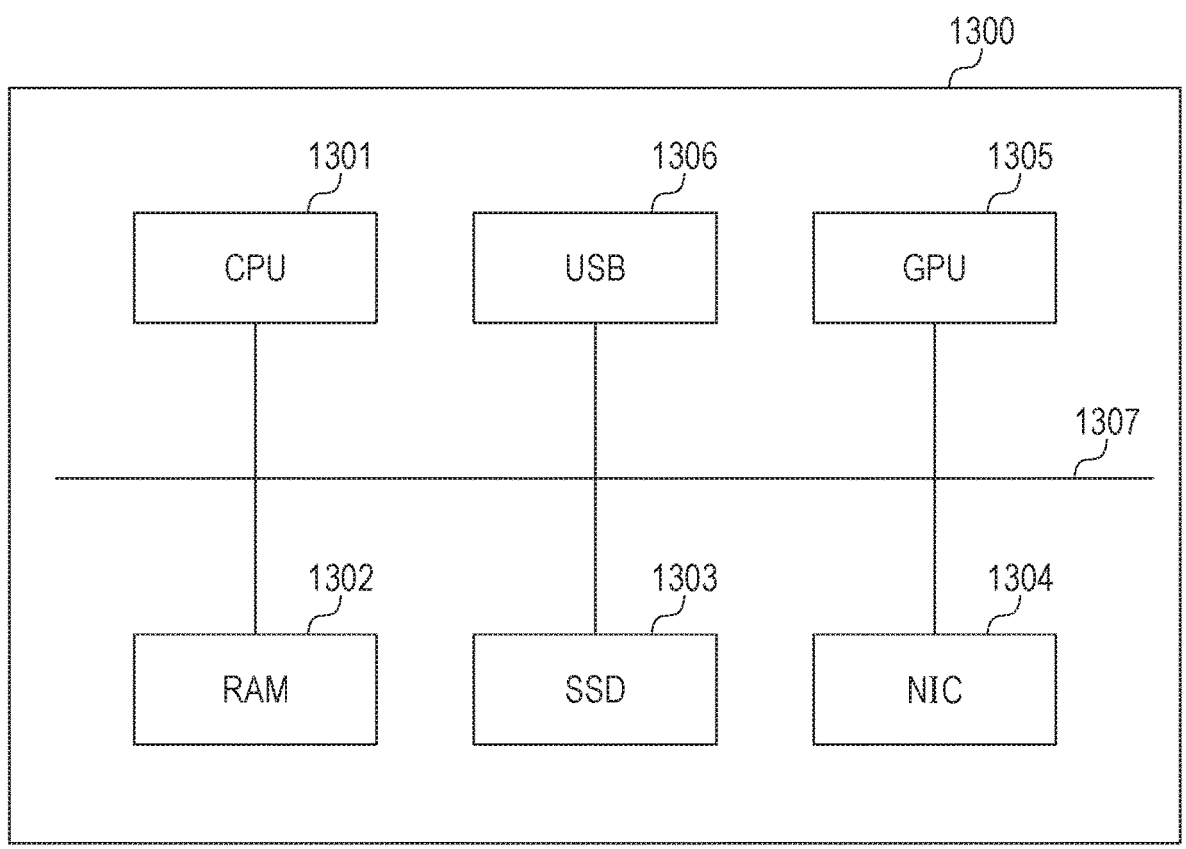
FIG. 13 is a diagram illustrating a configuration of hardware of a diagnostic imaging support apparatus or an image processing apparatus according to the exemplary embodiments.

A configuration of hardware of the diagnostic imaging support apparatus 10 or the image processing apparatus 50 indicated in the first to fourth exemplary embodiments described above will be described with reference to FIG. 13. The diagnostic imaging support apparatus 10 or the image processing apparatus 50 is realized by an information processing apparatus (computer) 1300 which has a CPU (Central Processing Unit) 1301, a RAM (Random Access Memory) 1302, an SSD (Solid State Drive) 1303, an NIC (Network Interface Card) 1304, a GPU (Graphics Processing Unit) 1305, a USB (Universal Serial Bus) 1306, and a bus 1307 for connecting them. In the SSD 1303, three-dimensional images according to the exemplary embodiments described above, information associated with images, various information of objects, medical information, and the like are stored, and further, a software program for realizing the processing illustrated in the flowcharts of FIGS. 5, 7, 9, and 11 above is stored. Such a software program is developed to the RAM 1302 by the CPU 1301. When the CPU 1301 executes a plurality of commands obtained by developing the software program, the processing illustrated in the flowcharts of FIGS. 5, 7, 9, and 11 above is realized.

The NIC 1304 is an interface unit used to allow connection with the network 20, and communicates with other apparatuses on the network 20 through the NIC 1304. The GPU 1305 is a unit for performing image processing. For example, the segmentation processing for dividing a region of a three-dimensional image obtained by imaging of a brain into a plurality of image regions corresponding to a plurality of anatomical regions, and the registration processing may be performed by the GPU 1305. The USB 1306 is an interface through which an operation unit, for example, such as a mouse or a keyboard is connected. For example, when a monitor of a touch-panel type is used as a display unit and the operation unit, the connection is achieved by the monitor of the touch-panel type, the GPU 1305, and the USB 1306. Display data is transmitted to the monitor from the information processing apparatus 1300 through the GPU 1305 and operation input data is transmitted to the information processing apparatus 1300 from the monitor through the USB 1306.

The diagnostic imaging support apparatus 10 or the image processing apparatus 50 is also able to realize similar functions by an information processing system including a plurality of information processing apparatuses connected through the network. In a diagnosis support system or an image processing system in this case, for example, a function of the image registration unit 12 associated with image processing and other functions may be realized by different information processing apparatuses. Further, the information processing apparatus which executes the function of the image registration unit 12 may be commonly used to the plurality of information processing apparatuses which execute other functions. In another example, the display control unit 14 may transmit for display medical case information obtained by searching to the display unit which is connected through the network 20.

The information processing apparatuses included in the information processing system are not required to exist in the same institution or the same country.

According to the exemplary embodiments above, it is possible to confirm abnormality in each of a plurality of anatomical regions in a brain by using captured images of the brain, and present reference information for diagnosis.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment (s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While aspects of the present invention have been described with reference to exemplary embodiments, it is to be understood that the aspects of the invention are not limited to the disclosed exemplary embodiments. The scope of the following claims is to be accorded the broadest interpretation so as to encompass all such modifications and equivalent structures and functions.

What is claimed is:

1. A diagnosis support system, comprising:
a processor; and
a memory coupled to the processor and having stored thereon instructions to be executed by the processor;
wherein the processor and the memory cooperate to act as:
an acquisition unit configured to acquire first tomographic image data and second tomographic image data;
a subtracted image generation unit configured to generate subtracted image data by performing subtraction between the first tomographic image data and the second tomographic image data;
a projection image generation unit configured to generate projection image data, in which a subject to be imaged rotates with a first direction as a rotation axis, by performing projection processing in a second direction on the subtracted image data generated by performing subtraction between the first tomographic image data and the second tomographic image data, wherein the second direction substantially perpendicular to the first direction corresponding to a stacking direction in which a plurality of cross-sectional images forming at least one of the first tomographic image data and the second tomographic image data are stacked is set as a direction of a sight line; and
a display control unit configured to display a projection image based on the projection image data generated by performing projection processing in the second direction on the subtracted image data; and
an operation unit configured to set a coordinate on the projection image,
wherein the display control unit displays, at the same time, the projection image generated by performing the projection processing in the second direction on the subtracted image data, a first cross-sectional image of the first tomographic image data corresponding to the coordinate set by the operation unit on the projection image, and a second cross-sectional image of the second tomographic image data corresponding to the coordinate set by the operation unit on the projection image, and
wherein the projection image is non-axial section, and the first cross-sectional image and the second cross-sectional image are axial section.

2. The diagnosis support system according to claim 1, wherein the display control unit displays the first cross-sectional image of the first tomographic image data, the second cross-sectional image of the second tomographic image data and the projection image based on the projection image data by performing projection processing on the subtracted image data on a same screen.

3. The diagnosis support system according to claim 1, wherein the display control unit updates the first cross-sectional image of the first tomographic image and the second cross-sectional image of the second tomographic image in a case where the operation unit changes the coordinate on the projection image.

4. The diagnosis support system according to claim 1, wherein the processor and the memory cooperate to further act as an operation unit configured to set the second direction.

5. The diagnosis support system according to claim 3, wherein the display control unit switches the first cross-sectional image of the first tomographic image and the second cross-sectional image of the second tomographic image simultaneously in a case where a drag operation is performed in a predetermined direction on the projection image.

6. The diagnosis support system according to claim 1, wherein, in a case where the operation unit places a pointer on the projection image, the display control unit does not update the projection image.

7. The diagnosis support system according to claim 1, wherein a plane direction of the first cross-sectional image and the second cross-sectional image is different from a plane direction of a projection plane of the projection image based on the projection image data by performing projection processing on the subtracted image data.

8. The diagnosis support system according to claim 1, wherein the display control unit displays the projection image based on the projection image data while rotating the projection image around a predetermined rotation axis.

9. The diagnosis supporting system according to claim 1, wherein the projection image generation unit changes the second direction at a predetermined time interval and generates a projection image, and wherein the display control unit displays the projection image corresponding to the changed direction.

10. The diagnosis support system according to claim 1, wherein the processor and the memory cooperate to further act as an image registration unit configured to perform image registration processing for deforming one or both of the first tomographic image data and the second tomographic image data.

11. The diagnosis support system according to claim 1, wherein the projection image of the non-axial section is substantially perpendicular to the first cross-sectional image and second cross-sectional image of the axial section.

12. An information processing method, comprising:
acquiring first tomographic image data and second tomographic image data;
generating subtracted image data by performing subtraction between the first tomographic image data and the second tomographic image data;
generating projection image data, in which a subject to be imaged rotates with a first direction as a rotation axis, by performing projection processing in a second direction on the subtracted image data generated by performing subtraction between the first tomographic image data and the second tomographic image data, wherein the second direction substantially perpendicular to the first direction corresponding to a stacking direction in which a plurality of cross-sectional images forming at least one of the first tomographic image data and the second tomographic image data are stacked is set as a direction of a sight line; and displaying a projection image based on the projection image data generated by performing projection processing in the second direction on the subtracted image data, wherein the displaying includes displaying, at the same time, the projection image generated by performing projection processing in the second direction on the subtracted image data, a first cross-sectional image of the first tomographic image data corresponding to the coordinate set on the projection image by the setting, and a second cross-sectional image of the second tomographic image data corresponding to the coordinate set on the projection image by the setting, and wherein the projection image is non-axial section, and the first cross-sectional image and the second cross-sectional image are axial section.

13. A non-transitory computer-readable recording medium in which a program for causing a computer to execute an information processing method is stored, the information processing method comprising:

acquiring first tomographic image data and second tomographic image data;

generating subtracted image data by performing subtraction between the first tomographic image data and the second tomographic image data;

generating projection image data, in which a subject to be imaged rotates with a first direction as a rotation axis, by performing projection processing in a second direction on the subtracted image data generated by performing subtraction between the first tomographic image data and the second tomographic image data, wherein the second direction substantially perpendicular to the first direction corresponding to a stacking direction in which a plurality of cross-sectional images forming at least one of the first tomographic image data and the second tomographic image data are stacked is set as a direction of a sight line;

displaying a projection image based on the projection image data generated by performing projection processing in the second direction on the subtracted image data; and setting a coordinate on the projection image based on the projection image data generated by performing projection processing in the second direction on the subtracted image data, wherein the displaying includes displaying, at the same time, the projection image generated by performing projection processing in the second direction on the subtracted image data, a first cross-sectional image of the first tomographic image data corresponding to the coordinate set on the projection image by the setting, and a second cross-sectional image of the second tomographic image data corresponding to the coordinate set on the projection image by the setting, and wherein the projection image is non-axial section, and the first cross-sectional image and the second cross-sectional image are axial section.

14. A diagnosis support system, comprising:

a processor; and a memory coupled to the processor and having stored thereon instructions to be executed by the processor;

wherein the processor and the memory cooperate to act as:

an acquisition unit configured to acquire first tomographic image data and second tomographic image data;

a subtracted image generation unit configured to generate subtracted image data by performing subtraction between the first tomographic image data and the second tomographic image data;

a projection image generation unit configured to generate projection image data, in which a subject to be imaged rotates with a first direction as a rotation axis, by performing projection processing in a second direction on the subtracted image data generated by performing subtraction between the first tomographic image data and the second tomographic image data, wherein the second direction substantially perpendicular to the first direction corresponding to a stacking direction in which a plurality of cross-sectional images forming at least one of the first tomographic image data and the second tomographic image data are stacked is set as a direction of a sight line;

a display control unit configured to display a projection image based on the projection image data generated by performing projection processing in a second direction on the subtracted image data; and an operation unit configured to set a coordinate on the projection image based on the projection image data generated by performing projection processing in a second direction on the subtracted data, wherein the display control unit displays, at the same time, the projection image generated by performing projection processing in a second direction on the subtracted image data, a first cross-sectional image of the first tomographic image data corresponding to the coordinate set on the projection image by the operation unit, and a second cross-sectional image of the second tomographic image data corresponding to the coordinate set on the projection image by the operation unit, wherein the projection image is non-axial section, and the first cross-sectional image and the second cross-sectional image are axial section, and wherein the second direction is substantially orthogonal to a third direction corresponding to a surface normal to the first cross-sectional image and the second cross-sectional image.

* * * * *